(12) United States Patent
Reed et al.

(10) Patent No.: US 9,316,612 B2
(45) Date of Patent: Apr. 19, 2016

(54) REGENERATIVE NANOSENSOR DEVICES

(71) Applicant: YALE UNIVERSITY, New Haven, CT (US)

(72) Inventors: Mark A. Reed, Monroe, CT (US); Xuexin Duan, West Haven, CT (US); Nitin Rajan, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/147,095

(22) Filed: Jan. 3, 2014

(65) Prior Publication Data

US 2014/0191186 A1 Jul. 10, 2014

Related U.S. Application Data

(60) Provisional application No. 61/749,006, filed on Jan. 4, 2013.

(51) Int. Cl.
*G01N 27/414* (2006.01)

(52) U.S. Cl.
CPC ........ *G01N 27/4145* (2013.01); *G01N 27/4146* (2013.01)

(58) Field of Classification Search
CPC .............. H01L 41/193; H01L 51/0098; H01L 51/0595
USPC ................... 977/702, 707, 720, 762
See application file for complete search history.

(56) References Cited

U.S. PATENT DOCUMENTS

| 4,661,444 | A | 4/1987 | Li |
| 7,005,711 | B2 | 2/2006 | King |
| 7,977,247 | B2 | 7/2011 | Black et al. |
| 2003/0124614 | A1 | 7/2003 | Utku et al. |
| 2004/0067530 | A1* | 4/2004 | Gruner ............................ 435/7.1 |
| 2004/0136866 | A1 | 7/2004 | Pontis |
| 2005/0079659 | A1 | 4/2005 | Duan et al. |
| 2005/0128788 | A1 | 6/2005 | Segal et al. |
| 2007/0048180 | A1 | 3/2007 | Gabriel et al. |
| 2007/0096164 | A1 | 5/2007 | Peters |
| 2007/0178477 | A1 | 8/2007 | Joiner, Jr. et al. |
| 2007/0231790 | A1 | 10/2007 | Su et al. |
| 2008/0287638 | A1* | 11/2008 | Reynolds et al. ............... 528/59 |
| 2010/0184104 | A1 | 7/2010 | Fahmy et al. |
| 2010/0260745 | A1 | 10/2010 | Zhou et al. |
| 2010/0297608 | A1 | 11/2010 | Stern et al. |
| 2011/0083678 | A1* | 4/2011 | Duan et al. ..................... 131/275 |

FOREIGN PATENT DOCUMENTS

| WO | WO 2010/099318 | 9/2010 |
| WO | WO 2012/125727 | 9/2012 |

OTHER PUBLICATIONS

Stern et al., 2008, IEEE Trans. Electron Devices, 55: 3119-3130.
Curreli et al., 2008, IEEE Trans. Nanotechnol., 7: 651-667.
(Continued)

*Primary Examiner* — Daniel Whalen
*Assistant Examiner* — Suberr Chi
(74) *Attorney, Agent, or Firm* — Riverside Law LLP

(57) ABSTRACT

The present invention provides a regenerative nanosensor device for the detection of one or more analytes of interest. In certain embodiments, the device comprises a nanostructure having a reversible functionalized coating comprising a supramolecular assembly. Controllable and selective disruption of the assembly promotes desorption of at least part of the reversible functionalized coating thereby allowing for reuse of the regenerative device.

12 Claims, 26 Drawing Sheets

(56) References Cited

OTHER PUBLICATIONS

Elfstrom et al., 2008, Nano Lett., 8: 945-949.
Gao et al., 2011, Nano Lett., 11: 3974-3978.
Park et al., 2007, Biosens. Bioelectron., 22: 2065-2070.
Bunimovich et al., 2006, J. Am. Chem. Soc.,128: 16323-16331.
Zheng et al., 2005, Nat. Biotechnol., 23: 1294-1301.
Hakim et al., 2012, Nano Lett.,12: 1868-1872.
Duan et al., 2012, Nat. Nanotechnol., 7: 401-407.
Ishikawa et al., 2009, ACS Nano, 3: 1219-1224.
Cui et al., 2001, Science, 291: 851-853.
Stern et al., 2007, Nature, 445: 519-522.
Gong, 2010, Small, 6: 967-973.
Lee et al., 2010, Nanomedicine, 6: 78-83.
Stern et al., 2010, Nat. Nanotechnol., 5: 138-142.
Fritz et al., 2002, Proc. Natl. Acad. Sci. U.S.A., 99: 14142-14146.
Milovic et al., 2006, Proc. Natl. Acad. Sci. U.S.A., 103: 13374-13379.
Jonkheijm et al., 2008, Angew. Chem., Int. Ed., 47: 9618-9647.
Nicu et al., 2008, J. Appl. Phys., 104: 111101-111116.
Duan et al., 2013, ACS Nano, 7(5): 4014-4021.
Mulder et al., 2004, Org. Biomol. Chem., 2: 3409-3424.
Elemans et al., 2009, Angew. Chem., Int. Ed., 48: 7298-7332.
Ludden et al., 2006, Chem. Soc. Rev., 35: 1122-1134.
Huskens et al., 2002, Angew. Chem., Int. Ed., 41: 4467-4471.
Davis et al., 2004, Nat. Rev. Drug Discovery, 3: 1023-1035.
Houk et al., 2003, Angew. Chem., Int. Ed., 42: 4872-4897.
Chen et al., 2010, Chem. Soc. Rev., 39: 495-505.
Ludden et al., 2006, Small, 2: 1192-1202.
Ludden et al., 2007, Angew. Chem., Int. Ed., 46: 4104-4107.
Ashton et al., 1996, J. Org. Chem., 61: 903-908.
Onclin et al., 2004, Langmuir, 20: 5460-5466.
Mulder et al., 2005, Small, 1: 242-253.
Myszka, 1997, Curr. Opin. Biotechnol., 8: 50-57.
Ishikawa et al, 2009, ACS Nano, 3: 3969-3976.
Vacic et al., 2011, Biosens. Bioelectron., 28: 239-242.
Chang et al., 2011, ACS Nano, 5: 9883-9891.
Stern et al., 2010, Small, 6(2): 232-238.

\* cited by examiner

REGENERATIVE NANOSENSOR DEVICES

CROSS-REFERENCE TO RELATED APPLICATIONS

This application claims priority to U.S. Provisional Application Ser. No. 61/749,006 filed Jan. 4, 2013, the contents of which are incorporated by reference herein in their entirety.

STATEMENT REGARDING FEDERALLY SPONSORED RESEARCH OR DEVELOPMENT

This invention was made with government support under EB008260 and GMO22778 awarded by the National Institute of Health and under HDTRA1-10-1-0037 awarded by the Defense Threat Reduction Agency. The government has certain rights in the invention.

BACKGROUND OF THE INVENTION

In recent years, there has been a surge of interest in exploiting biosensing systems based on CMOS-compatible silicon nanowire field-effect transistors (NWFETs) (Stern et al., 2008, IEEE Trans. Electron Devices, 55: 3119-3130; Curreli et al., 2008, IEEE Trans. Nanotechnol., 7: 651-667; Elfstrom et al., 2008, Nano Lett., 8: 945-949; Gao et al., 2011, Nano Lett., 11: 3974-3978). Silicon nanowires (Si-NWs) modified with specific surface receptors present a powerful detection platform for a broad range of biological and chemical species. The small diameter of NWFET devices provides extremely high sensitivity because the binding of target molecules causes accumulation/depletion of carriers throughout the wire cross-section, enabling label-free, real-time detection and monitoring of biomolecular interactions (Park et al., 2007, Biosens. Bioelectron., 22: 2065-2070; Bunimovich et al., 2006, J. Am. Chem. Soc., 128: 16323-16331; Zheng et al., 2005, Nat. Biotechnol., 23: 1294-1301; Hakim et al., 2012, Nano Lett., 12: 1868-1872; Duan et al., 2012, Nat. Nanotechnol., 7: 401-407; Ishikawa et al., 2009, ACS Nano, 3: 1219-1224; Cui et al., 2001, Science, 291: 851-853; Stern et al., 2007, Nature, 445: 519-522; Gong, 2010, Small, 6: 967-973; Lee et al., 2010, Nanomedicine, 6: 78-83). Although such devices were first demonstrated by chemically synthesized VLS NWs (Cui et al., 2001, Science, 291: 851-853), top-down fabricated CMOS-compatible Si-NW devices offer advantages of high yield, exceptional uniformity, and system-level integration and multiplexing (Steprn et al., 2007, Nature, 445: 519-522). Within the past few years, many of the previous limitations to charge-based affinity sensors, such as charge screening and sensor drift, have been solved (Steprn et al., 2010, Nat. Nanotechnol., 5: 138-142; Fritz et al., 2002, Proc. Natl. Acad. Sci. U.S.A., 99: 14142-14146; Milovic et al., 2006, Proc. Natl. Acad. Sci. U.S.A., 103: 13374-13379). In addition, the ability to multiplex electronic sensors for higher accuracy and false positive/negative elimination has become an attractive benefit of the approach. NWFETs not only represent an attractive technology for future miniaturized and multiplexed biosensing platforms but could also be extended to high-throughput functional assays (e.g., drug screening).

In order to detect bimolecular interactions, receptor molecules (e.g., proteins or protein-binding ligands) are immobilized on the Si NWFET surface, and the target (bio)molecules are recognized through specific binding. The performance of biosensors, specifically the sensitivity, specificity, reusability, chemical stability, and reproducibility, is critically dependent on the (bio)functionalization of the sensor platform. The type of linkers used for the immobilization of the capture probes and the exact immobilization protocols play a vital role in the overall performance of sensors (Jonkheijm et al., 2008, Angew. Chem., Int. Ed., 47: 9618-9647). Currently, the commonly used strategy for immobilization is attaching the receptor molecules to the nanowire surface via a covalent approach through amino silanization of the Si/SiO$_2$ surface, followed by amine coupling (Gao et al., 2011, Nano Lett., 11: 3974-3978; Nicu et al., 2008, J. Appl. Phys., 104: 111101-111116). Such covalent attachment has disadvantages, such as autoxidation of amine-functionalized surfaces, which could limit long-term device application, lack of control of molecule placement and conformation (with a potential reduction in activity), and increasing heterogeneity in the population of immobilized species. Most importantly, such attachment is irreversible, and functionalized devices can be (practically) used only once, an issue that has limited this approach for applications.

Thus, there is a need in the art for sensor systems and devices with improved probe immobilization. The present invention satisfies this unmet need.

SUMMARY OF THE INVENTION

The present invention provides a regenerative nanosensor device comprising a nanostructure forming an electrically conducting pathway between at least a first contact and a second contact, the nanostructure surface having a reversible coating comprising a reversible functionalized supramolecular assembly. In one embodiment, the nanostructure is fabricated on a substrate. In one embodiment, the substrate is a semiconductor substrate or a semiconductor-on-insulator (SOI) substrate. In one embodiment, the nanostructure is a nanowire, a nanoribbon, or a carbon nanotube. In one embodiment, the first and second contacts form a source and a drain contact, respectively.

In one embodiment, the device further comprises at least one solution chamber positioned atop at least a portion of the nanostructure such that the contents of the solution chamber are accessible to the nanostructure. In one embodiment, the device further comprises at least one inlet and at least one outlet for delivering a fluid sample to the solution chamber.

In one embodiment, the coating comprises a self-assembled monolayer (SAM) atop of the nanostructure surface. In one embodiment, the coating comprises a linker layer bound to the SAM.

In one embodiment, the SAM comprises β-cyclodextrin (β-CD), thereby providing a β-CD SAM. In one embodiment, the SAM comprises a polyelectrolyte film.

In one embodiment, the linker layer comprises a linker comprising a receptor molecule which specifically binds to an analyte of interest. In one embodiment, the linker comprises a chain region which prevents non-specific binding to the nanostructure. In one embodiment, the chain region comprises oligo(ethylene glycol) (OEG).

In one embodiment, the linker comprises a guest moiety which reversibly binds to the SAM. In one embodiment, the guest moiety comprises adamantane.

The present invention also provides a method of manufacturing a regenerative nanosensor device. The method comprises providing a device comprising a nanostructure forming an electrically conducting pathway between at least a first contact and a second contact, and forming a reversible coating comprising a reversible functionalized supramolecular assembly atop the surface of the nanostructure.

In one embodiment, the nanostructure is fabricated on a substrate. In one embodiment, the substrate is a semiconductor substrate or a semiconductor-on-insulator (SOI) substrate. In one embodiment, the nanostructure is a nanowire, a nanoribbon, or a carbon nanotube. In one embodiment, the first and second contacts form a source and a drain contact, respectively.

In one embodiment, forming the reversible coating comprises applying a self-assembled monolayer (SAM) atop the surface of a nanostructure. In one embodiment, the method comprises contacting the nanostructure with β-cyclodextrin (β-CD), thereby providing a β-CD SAM. In one embodiment, the SAM comprises a polyelectrolyte thin film.

In one embodiment, forming the reversible coating further comprises forming a linker layer atop the SAM. In one embodiment, forming the reversible coating further comprises contacting the SAM with a linker comprising a receptor molecule and a guest moiety, which reversibly binds to the SAM.

In one embodiment, forming the reversible coating further comprises forming a linker layer atop the β-CD SAM by contacting the β-CD SAM with a linker comprising a receptor molecule and a guest moiety comprising adamantane, which reversibly binds to the β-CD SAM.

The present invention also provides a method of replacing a receptor molecule functionalized on the nanostructure of a regenerative nanosensor device. The method comprises providing a regenerative nanosensor device comprising a nanostructure forming an electrically conducting pathway between at least a first contact and a second contact, the nanostructure surface having a first coating comprising a reversible functionalized supramolecular assembly comprising a first receptor molecule, and disrupting the supramolecular assembly of the first coating to induce the selective removal of at least one layer of the first coating, thereby forming an unfunctionalized nanostructure. In one embodiment, the method comprises coating the unfunctionalized nanostructure with a second coating comprising a reversible functionalized supramolecular assembly comprising a second receptor molecule.

In one embodiment, the coating comprises a SAM.

In one embodiment, the SAM comprises β-cyclodextrin (β-CD), thereby providing a β-CD SAM.

In one embodiment, the coating comprises a linker layer comprising a linker comprising a receptor molecule. In one embodiment, the linker comprises a chain region which prevents non-specific binding to the nanostructure. In one embodiment, the linker comprises a guest moiety which reversibly binds to the SAM. In one embodiment, the chain region comprises oligo(ethylene glycol) (OEG). In one embodiment, the guest moiety comprises adamantane. In one embodiment, disrupting the supramolecular assembly of the first coating comprises administering a solution to the device, wherein the solution comprises β-CD to induce the desorption of the linker from the SAM.

In one embodiment, the SAM comprises a polyelectrolyte thin film. In one embodiment, disrupting the supramolecular assembly of the first coating comprises altering the pH of a solution surrounding the nanostructure to induce the desorption of the polyelectrolyte thin film.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1D, is a schematic illustrating an exemplary scheme for the regeneration of one embodiment of the device of the invention. The functionalized nanostructure (FIG. 1A) is used to detect an analyte of interest via binding to a receptor molecule (FIG. 1B). The functionalized coating of the nanostructure can be selectively removed by disrupting the binding within a supramolecular assembly of the coating (FIG. 1C). The device is regenerated by subsequently adding a new functionalization to the nanostructure by re-establishing the supramolecular assembly (FIG. 1D).

FIG. 3A and FIG. 3B, depicts a set of images of an exemplary device and an exemplary functionalization scheme of the device. (FIG. 3A) Optical and SEM images of the Si NWFETs. (FIG. 3B) Process scheme of the functionalization of Si-NWs with β-CD.

FIG. 4, comprising (FIG. 4A) Chemical structures of d- and l-thyroxine. (FIG. 4B) Real-time sensor responses of 1 nM d- and l-thyroxine and their mixtures binding and unbinding on β-CD-functionalized Si NWFETs. The real-time concentration titrations of (FIG. 4C) d- and (FIG. 4D) l-thyroxine. The arrows indicate the time at which the concentration of thyroxine is increased. Insets: Calibrated titration curve of (FIG. 4C) d- and (FIG. 4D) l-thyroxine. The error bar is obtained by the average of all data points except the transitions of each concentration. The affinity constants were obtained by fitting the titration curve with a Langmuir isotherm (red line). For all measurements 1 mM sodium carbonate buffer (pH 10.5) was used.

FIG. 5, comprising (FIG. 5A) Chemical structures of the adamantane-terminated guest compounds. Real-time sensor responses of the adsorption and desorption of (FIG. 5B) monovalent 1 (10 μM) and (FIG. 5C-FIG. 5D) divalent guest molecule 2 (0.1 μM) on β-CD-functionalized Si-NW FETs. For all measurements, 1 mM sodium carbonate buffer (pH 10.5) was used.

FIG. 6, comprising (FIG. 6A) Chemical structures of the divalent adamantyl-biotin linker 3 and adamantyl-oligo(ethylene glycol) 4 and adsorption scheme for the sensing of SAv at β-CD SAMs through a mixture of 3 and 4. (FIG. 6B) Real-time sensorgrams of the adsorption and desorption of 2 nM SAv through the mixture of 3 and 4 (5 μM, ratio 1:5) on β-CD-functionalized Si NWFETs. Symbols indicate switching of solutions in the flow cell: divalent linker (*), SAv (↓), and 8 mM β-CD solution (↑). For all measurements, 1 mM HEPES buffer (pH 7.4) was used.

FIG. 10, comprising (FIG. 10C) Control experiments on isothiocynate functionalized surface.

FIG. 12, comprising (FIG. 12A) Chemical structures of the divalent adamantly-biotin linker 3, and adsorption scheme for the sensing of SAv at β-CD SAMs through the divalent linker 3. (FIG. 12B) Real-time sensorgrams of the adsorption and attempted desorption of 2 nM of SAv through divalent linker 3 (5 µM). Symbols indicate switching of solutions in the flow cell: divalent linker (*), SAv (↓), and 8 mM β-CD solution (↑). For all measurements, 1 mM HEPES buffer (pH 7.4) was used.

DETAILED DESCRIPTION

Figure 1:
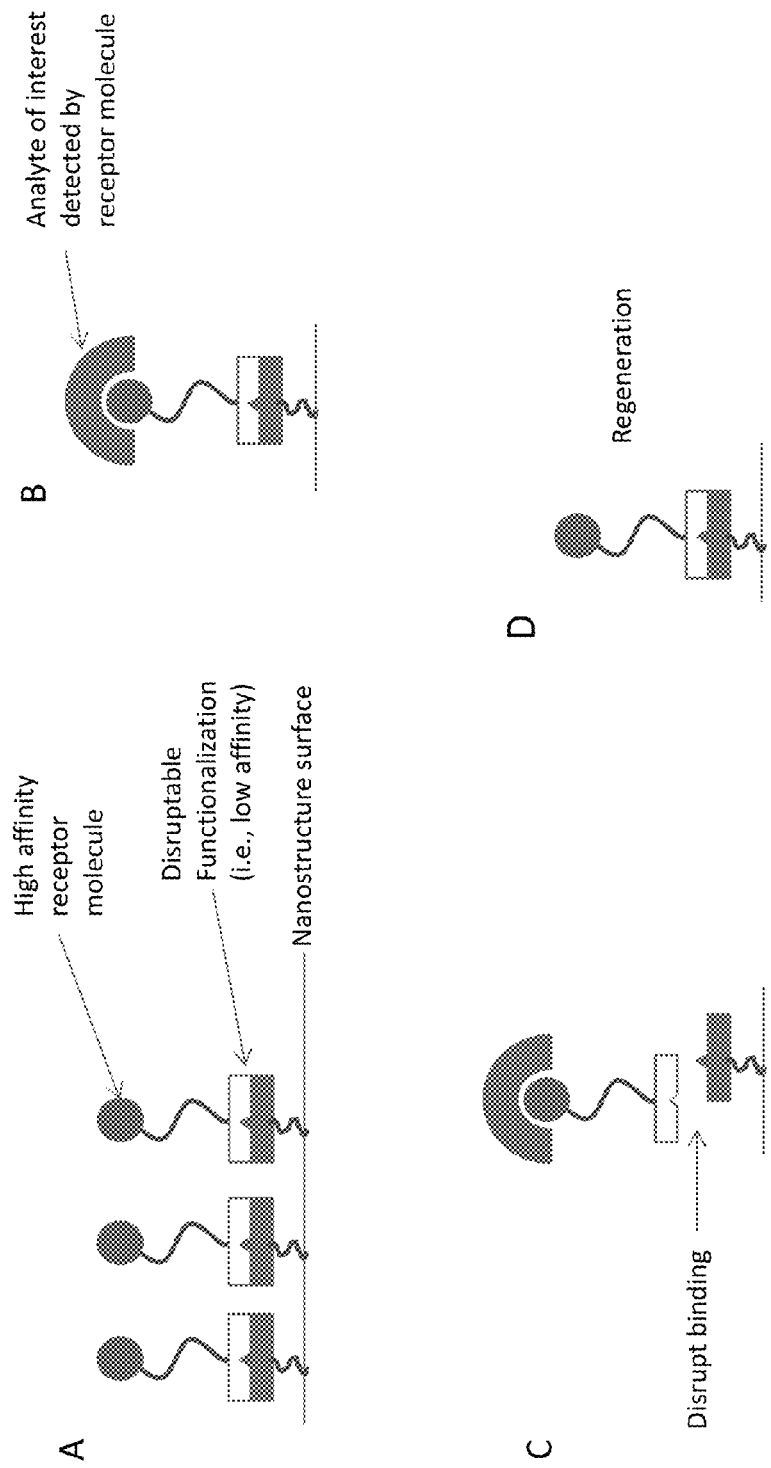
FIG. 1, comprising

The present invention relates to regenerative biosensor devices. The devices described herein comprise nanostructures having a reversible functionalized coating which allows for detection of an analyte of interest. The reversible coating also allows for the devices to be regenerative as at least a portion of the coating may be controllably and selectively removed from the nanostructure surface, allowing for the device to be reused. Importantly, the adsorption and desorption of the coating, or portion thereof, does not result in the degradation of the nanostructure, thereby allowing for reusing of the device without compromising the integrity or performance of the sensing device.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "physiological solution" refers to any solution comprising physiological material isolated from a living organism. Non-limiting examples of physiological materials contemplated within the invention are blood, blood subfractions, serum, lymphatic fluid, saliva, urine, sweat, vaginal fluid and sperm. In one embodiment, the physiological solution comprises material selected from the group consisting of blood, blood subfractions, serum, lymphatic fluid, saliva, urine, sweat, vaginal fluid and sperm. In another embodiment, the physiological solution comprises blood.

As used herein, the term "sample" or "test sample" refers to a material to be analyzed by the sensors of the invention. For example, the sample contains some property that is to be detected by the sensor. In one embodiment, a sample comprises a physiological solution. In another embodiment, a sample can be derived from physiological material isolated from a living organism. The sample may contain any material suitable for detecting the desired analytes, and may comprise cellular and/or non-cellular material obtained from an organism.

An "analyte", as used herein refers to any substance or chemical constituent that is undergoing analysis. For example, an "analyte" can refer to any atom and/or molecule; including their complexes and fragment ions. The term may refer to a single component or a set of components. In the case of biological molecules/macromolecules, such analytes include but are not limited to: polypeptides, polynucleotides, proteins, peptides, antibodies, DNA, RNA, carbohydrates, steroids, and lipids, and any detectable moiety thereof, e.g. immunologically detectable fragments. In one embodiment, the analyte is contained within the sample applied to the sensors of the invention. In one embodiment, the sensors determine the amount, concentration, or presence of an analyte in a sample. An analyte can be a biomarker.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. Biomarkers also include any calculated indices created mathematically or combinations of any one or more of the foregoing measurements, including temporal trends and differences.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the polypeptides include natural peptides, recombinant peptides, synthetic peptides or a combination thereof. A peptide that is not cyclic has an N-terminus and a C-terminus. The N-terminus has an amino group, which may be free (i.e., as a $NH_2$ group) or appropriately protected (for example, with a BOC or a Fmoc group). The C-terminus has a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "antibody" refers to an immunoglobulin, whether natural or partly or wholly synthetically produced. The term also covers any polypeptide, protein or peptide having a binding domain that is, or is homologous to, an antibody binding domain. These may be isolated from natural sources, or may be partly or wholly synthetically produced. Examples of antibodies are intact immunoglobulin molecules, as well as fragments thereof, such as Fab, F(ab')2, Fv fragments, and single chain variable fragments (scFv), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of a Fab or other immunoglobulin expression library, and suitable derivatives.

As used herein, the term "specifically binds," referring to a receptor molecule binding to an analyte of choice, means that the receptor molecule binds the analyte of choice, or portion thereof, but does not bind to a molecule that is not the analyte of choice. Receptor molecules that specifically bind to an analyte of choice, or portions thereof, do not substantially cross-react with molecules outside the analyte of choice. Receptor molecules can include antibodies, antibody fragments, proteins, nucleotide sequences, and the like.

As used herein, a "polynucleotide" means a single strand or parallel and anti-parallel strands of a nucleic acid. Thus, a polynucleotide may be either a single-stranded or a double-stranded nucleic acid.

As used herein, the term "nucleic acid" typically refers to large polynucleotides.

As used herein, the term "oligonucleotide" typically refers to short polynucleotides, which are generally not greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, a "probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides devices, methods for their production, and methods of use, especially suited to sense a variety of molecular species, biological species, or cellular responses. In this manner, the species and/or analytes of interest may be detected and/or monitored.

The sensor device of the present invention comprises a nanostructure having reversible functionalized coating that allow for reuse of the device without sacrificing device performance. The reversible coating is based on a supramolecular assembly formed atop the nanostructure surface, which may be selectively disrupted to allow for the device to be reused. Controllable and selective disruption of the assembly promotes desorption of at least part of the reversible functionalized coating thereby allowing for reuse of the regenerative device. For example, in certain embodiments the coating is a multi-layer coating, where one or more layers of the coating may be controllable and selectively released from the nanostructure surface, thereby allowing for the future adsorption of the same or different functionalized coating and the reuse of the device for detection of the same or different species of interest.

Sensors and methods of fabrication have been previously described in U.S. patent application Ser. Nos. 12/517,230; 12/535,396; 12/680,833; and 14/005,056 and in International Patent Application PCT/US10/25412, the entire contents of which are incorporated by reference herein in their entirety.

For example, in one embodiment, the detection device is implemented as an elongated nanostructure, for example, a nanowire, and has an exposed surface that is substantially smooth and well defined. The nanostructure of the device is not limited to any particular type of nanostructure or any particular method of forming the nanostructure. Exemplary nanostructures include nanowires, nanotubes, nanoribbons, carbon nanotubes, extended gate field effect transistors, and the like. The nanostructure may be fabricated on a semiconductor substrate or on a semiconductor-on-insulator (SOI) substrate. Fabrication can comprise any techniques known in the art including but not limited to TMAH wet etching, plasma etching, sputter etching, reactive-ion etching (RIE), and the like. While the device described herein is exemplified using a nanostructure that is etched from a semiconductor layer, one skilled in the art shall recognize that the present device is not limited to "etched" nanostructures. Rather, the present invention encompasses any type of nanostructure, including those that are deposited or placed onto a substrate. For example, in certain embodiments, nanostructures are grown, using techniques such as chemical vapor deposition, vapor-liquid-solid method (VLS), and the like.

In certain embodiments, the exposed surface of the nanostructure used for detection is functionalized with one or more probes for detection of an analyte of interest, depending on the device's applications. For example, in one embodiment, the nanostructure comprises a reversible surface coating comprising at least one receptor molecule for detection of an analyte of interest.

Figure 15:
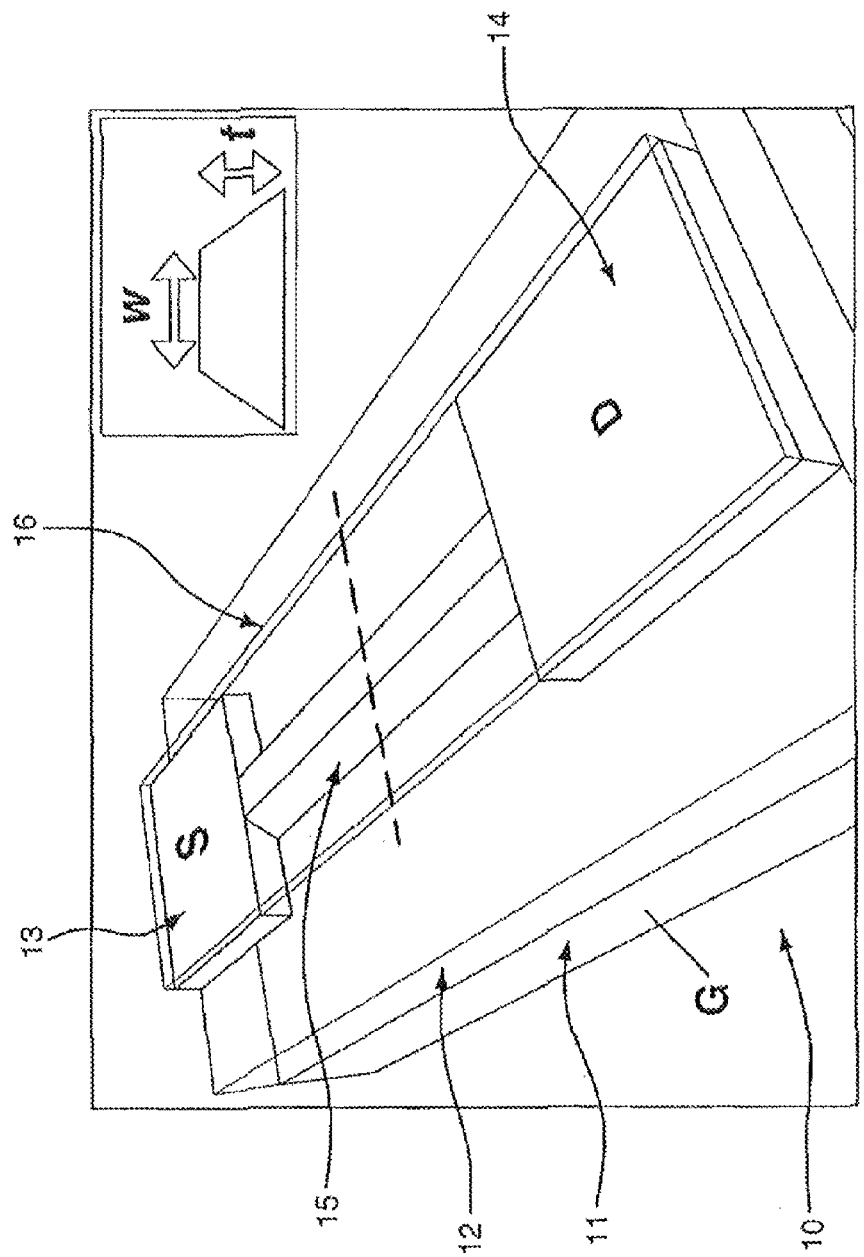
FIG. 15 shows a schematic diagram of an exemplary nanowire device, according to one embodiment of the invention, after anisotropic etching and before removal of the masking oxide.

FIG. 15 shows a schematic diagram of an exemplary nanostructure sensor device according to one embodiment of the invention. In this embodiment, the device is fabricated on a (100) silicon-on-insulator (SOI) wafer 10 which includes a silicon substrate 11, a thin $SiO_2$ layer 12 on the Si substrate 11 and a top Si layer on the $SiO_2$ layer 12, in which the source (S) contact 13, the drain (D) contact 14 and the actual nanostructure 15. Also shown is a $SiO_2$ layer 16 overlaying the contacts 13, 14 and nanostructure 15. The $SiO_2$ layer 16 in the illustrated example has a width of about 600 nm, from which the nanostructure with a final width w (see inset) is then etched. In the illustrated embodiment, nanostructure 15 is prepared from the top Si layer and the bottom surface of nanostructure 15 is therefore in direct material contact with the $SiO_2$ layer 12 and thus inaccessible.

The inset in FIG. 15 shows a cross-sectional view of nanostructure 15 with a trapezoidal shape of thickness t and width w defined by the processing steps. The sloped surfaces of the trapezoid represent the natural Si (111) planes, or cleavage planes, and, in one embodiment, may have an angle of about 54.7° between the (100) plane and the (111) plane.

The width of the nanostructure may be selected to optimize device sensitivity. As those skilled in the art will appreciate, the exemplary nanostructures form a conductive pathway between the contact regions 13 and 14 which, in the sensing operation, is affected by surface charges formed or deposited on or near the exposed lateral surfaces. These surface charges induce the greatest changes in the conductive pathway if they affect a substantial portion of the trapezoidal cross section of the device. The depth by which the surface charges extend from the exposed lateral surfaces inward is governed by the depletion width that in turn depends on the Debye length ($L_D$) of the semiconductor material from which the nanowire is formed. The semiconductor characteristic Debye length may be presented as:

$$L_D \equiv \sqrt{\frac{\varepsilon_s kT}{q^2 N_B}} \qquad (1)$$

wherein q is the electron or hole charge, $N_B$ is the doping density, T is the absolute temperature, and $\varepsilon_s$ is the dielctric constant of the semiconductor material. Exemplary values for $L_D$ at room temperature are $L_D \approx 100$ nm for $N_B = 10^{15}$ cm$^{-3}$, and $L_D \approx 10$ nm for $N_B = 10^{17}$ cm$^{-3}$. The values for $L_D$ of GaAs are identical to those of Si, whereas the values for Ge are greater by a factor of 1.16 due to the larger dielectric constant. The depletion width of the conduction nanowire pathway, which depends on the Debye length ($L_D$) of the semiconductor material, can be changed by applying a gate voltage to a gate contact. The gate contact may be the silicon layer 11, operating as a back gate, or another contact layer disposed above nanostructure 15, operating as a top gate (not shown). In another embodiment, gate voltage is applied by solution gating. In this case, the electrical potential of the solution serves to modify the carrier density in the device, which gives a transconductance value of the device that can be used to accurately determine the change in surface potential due to absorbed species of interest.

In further detail, the charge of solution-based molecules and macromolecules is screened by dissolved solution counterions: a negative species such as streptavidin or DNA will be surrounded by positively charged ions due to electrostatic interactions. Accordingly, molecular charge screening by dissolved solution counterions—Debye screening—on sensor response can be evaluated. At a characteristic Debye length ($\lambda_D$), the number of net positive charges approaches the number of negative charges on the protein or DNA. The result is a screening effect such that the electrostatic potential arising from charges on the protein or DNA decays exponentially toward zero with distance. For aqueous solutions at room temperature, this Deybe length ($\lambda_D$) may be re-written from its previously described equation and now presented as:

$$\lambda_D = \frac{1}{\sqrt{4\pi l_B \sum_i \rho_i z_i^2}}, \qquad (2)$$

where $I_B$ is the Bjerrum length=0.7 nm, $\Sigma_i$ is the sum over all ion species, and $\rho_i$ and $z_i$ are the density and valence, respectively, of ion species i. Thus, for optimized sensing, the Debye length must be carefully selected for NW-FET measurements since molecules binding to the devices are likely removed from the sensor surface by approximately 2-12 nm (the size of the receptor proteins or DNA linkers bound to the sensor surface).

Both boron-doped p-type devices and arsenic-doped n-type devices can be prepared. Fabrication of these complementary devices is compatible with conventional silicon CMOS processing. The sensor devices can therefore become part of an integrated system with on-chip signal processing, error detection, and complementary detection to avoid false positives. Complementary devices are useful for detecting, for example, small concentrations of antibodies.

The active region of the nanostructure may be between about 1 μm to about 100 μm long, with a thickness between about 25 nm to about 100 nm. In certain embodiments, the nanostructure has a width of about 1 nm to about 10 μm. In one embodiment, the nanostructure has a variable width through the thickness of the nanostructure, thereby giving the nanostructure a trapezoidal shape. In certain embodiments, the width at the top of the trapezoidal cross-section may be etched down to about 10 nm. In general, the thinner the active region of the nanowire, the larger its surface area-to-volume ratio.

In one embodiment of the present invention, the nanostructure of the sensors is a nanoribbon. Nanoribbons are devices with nanoscale thicknesses and microscale lateral dimensions (Elfstrom et al., Nano Lett. 8:945-949). While nanoribbons are often less sensitive than nanowire sensors, nanoribbons typically have significant fabrication and cost advantages. Fabricated from ultra-thin silicon-on-insulator (UT-SOI) wafers using conventional lithographic techniques, these devices have been demonstrated to detect streptavidin in the 0.0318-53 ng/mL range (Elfstrom et al., 2008, Nano Lett. 8:945-949), a sensitivity range ideally suited for cancer antigen detection. Nanoribbon fabrication has been described in International Patent Application PCT/US10/25412, the entire contents of which are incorporated by reference herein in their entirety.

In one embodiment, when the nanostructure is fabricated on an SOI wafer with the underlying silicon substrate operating as a back gate, a gate electrode can also be applied on top of the nanowire. In another embodiment, the gate electrode can also be inserted into a solution surrounding the nanostructure, thereby serving as a solution gate. Alternatively, the top silicon active layer can be insulated from the substrate by a reverse biased p-n junction. In an alternative embodiment, the nanowires may be formed in compound semiconductors, such as GaAs, GaAlAs, GaAlInAsP and other III-V compound semiconductors, or in any other materials that exhibit a low intrinsic surface state density that can be altered by an externally applied surface charge. As compound semiconductor layers with different composition respond differently to chemical etchants, the fabrication of devices in compound semiconductor materials may include the formation of etch stop layers which may be used to define the narrow dimensions of nanowires.

Figure 7:
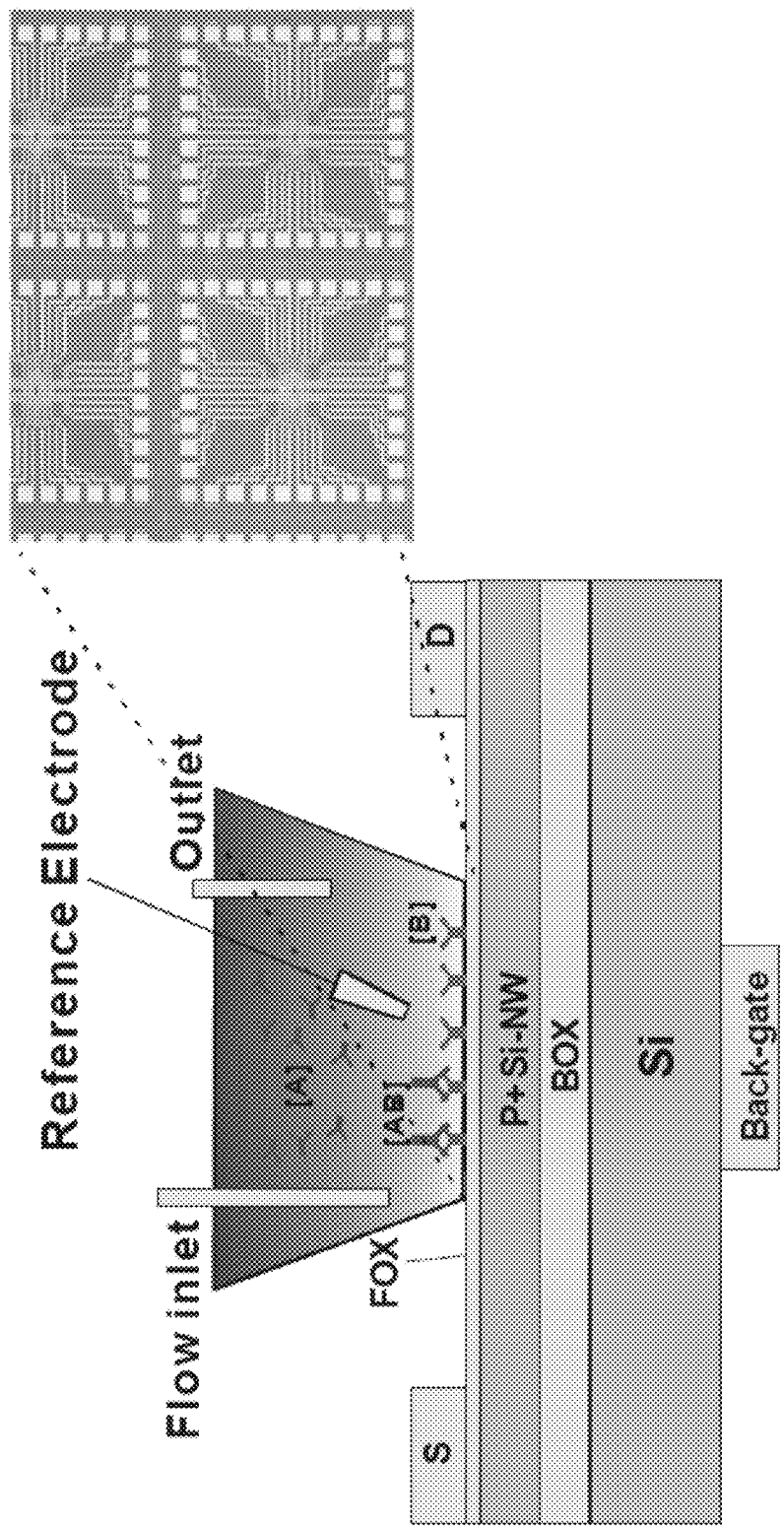
FIG. 7 is a schematic of an exemplary Si-NW-FET biosensor.

In certain embodiments, the sensor device of the invention comprises a macro-scale solution chamber. FIG. 7 illustrates an exemplary solution chamber configured to induce mixing of fluids that are continuously supplied to the nanostructure for solution-based electrical response measurement. These fluids may be a fluid sample being analyzed for the presence of an analyte of interest, a buffer, or a specific media that are conducive to cellular growth or homeostasis. In a preferred configuration, this solution chamber is designed to avoid the well-characterized limits on sensitivity and response time inherent in diffusion-limited systems, such as in microchannels. In one embodiment, the device comprises at least one flow inlet and at least one flow outlet positioned within the solution chamber to provide delivery and removal of a fluid to the fluid chamber. In certain embodiments, the device comprises a reference electrode insertable within the flow chamber.

The solution chamber may be manufactured of any suitable material including, for example plastics such as polytetrafluoroethylene (PTFE); photoresists, such as SU-8, elastomers, such as PDMS; or an etchable polymer thin film, such as paralyne. The solution chamber may be any suitable size or geometry that is sufficient to hold the volume of solution that may be needed for the particular application. For example, the solution chamber may cylindrical, rectangular, and the like. In one embodiment, the solution chamber is substantially cylindrical having a diameter of about 10 µm to about 1 cm. In one embodiment, the solution chamber is substantially cylindrical having a diameter of about 5 mm. In one embodiment, at least a portion of a bottom wall of the solution chamber is absent thereby allowing a solution housed in the solution chamber to be exposed to the underlying nanostructure. In one embodiment, the solution chamber is substantially sealed to limit the exposure of the chamber or solution to the environment. For example, the chamber may be substantially sealed such that the chamber interior is only accessible through the flow inlet or flow outlet. The flow inlet and/or flow outlet may be any suitable shape or size sufficient for the delivery and removal of solution. In certain embodiments, the flow inlet and/or flow outlet are smaller than the size of the solution chamber. For example, in one embodiment, the flow inlet and flow outlet have a diameter of about 0.5 mm. The flow inlet and flow outlet may be made of any suitable material or tubing known in the art. In one embodiment, the flow inlet is placed in the center of the chamber to allow for efficient mixing of the solution. The flow inlet and flow outlet may be connected to a fluidic delivery system, including, for example a syringe pump, to allow for the controllable delivery of one or more solutions to the nanostructure. In one embodiment, the fluidic delivery system comprises a valve, which may be manually or electrically controlled to switch the solution to be delivered.

Figure 2:
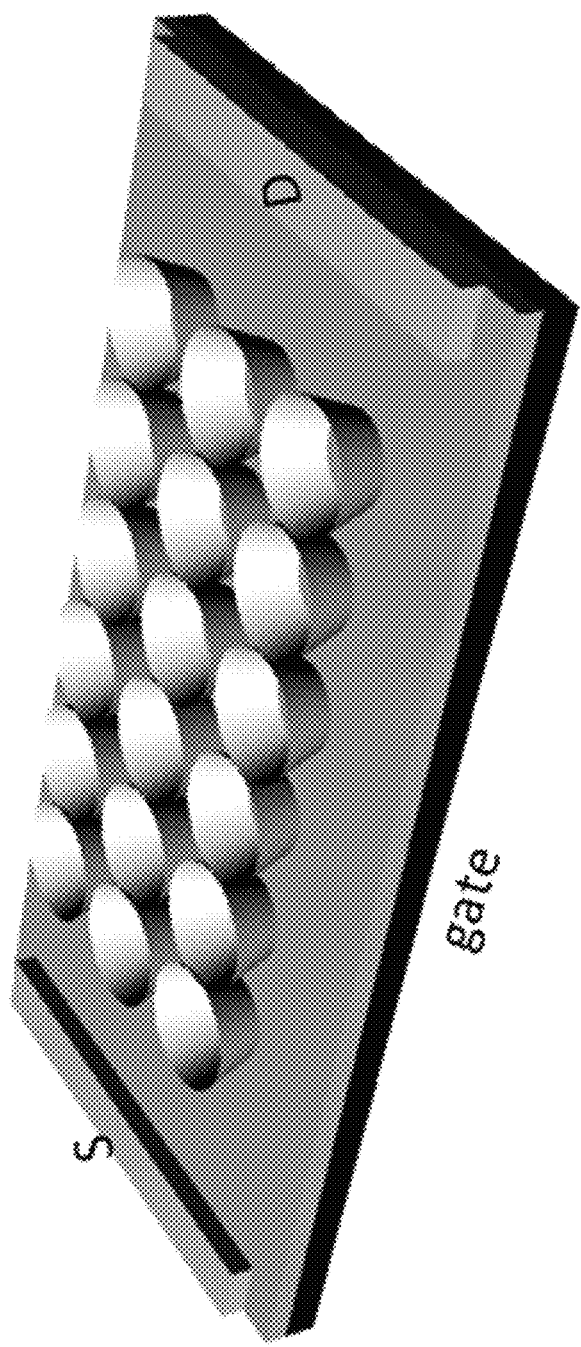
FIG. 2 is a drawing depicting an exemplary device of the invention.

In one embodiment, the device comprises a plurality of chambers, each chamber positioned over a discrete portion of a nanostructure (FIG. 2). This produces an array of chambers that may be used for simultaneous or complementary detection of one or more analytes of interest. In certain embodiments, one or more of the plurality of chambers may be fluidically connected, such that a solution removed from one chamber may be delivered to another chamber. In another embodiment, each of chambers is connected to its own fluidic delivery system.

As described herein, a nanosensor device of the invention may be functionalized by receptor molecules that bind to specific analytes of interest, in which case a conductance change occurs in the corresponding sensor device. Given a p-type nanostructure, its conductance is adapted to increase when a macromolecule with negative surface charge binds to a nanostructure surface functionalized with receptor molecules, whereas the opposite response occurs when a positively-charged molecular binding occurs on a functionalized device surface. Hence functionalized nanostructures are well suited for performing selective label-free sensing of macromolecules. In addition to p-type nanostructure functionalization, selective n-type nanostructure functionalization is equally viable for performing label-free sensing.

In certain embodiments, the device of the present invention is functionalized using a reversible multi-layer coating of the nanostructure. For example, the present invention is partly based upon a supramolecular functionalization approach in which multiple molecular layers are coated onto at least a portion of the nanostructure surface, and wherein one or more of the layers may be controllably removed from the nanostructure, thereby providing the ability to reuse the device for multiple applications.

For example, FIG. 1 depicts an exemplary scheme for the regeneration of a nanosensor device, where the functionalized coating of a nanostructure (FIG. 1A) is used to detect an analyte of interest via a receptor molecule that specifically binds the analyte (FIG. 1B). The functionalized coating may be selectively disrupted (FIG. 1C), and subsequently restored or regenerated (FIG. 1D) in order to reuse the sensor for the detection of the same or different analyte. In one embodiment, and as depicted in FIG. 1, the functionalized coating is disrupted by disrupting the binding between the molecule assembled on the nanostructure surface and a linker which reversibly binds to the molecule. That is, the binding between the linker and nanostructure coated molecule may be selectively and controllably exploited in order to functionalize the nanostructure with a receptor molecule, remove the receptor molecule, and/or add a new receptor molecule.

In one embodiment the reversible functionalized coating comprises a self-assembled monolayer (SAM) and a linker layer. For example, in one embodiment, the nanostructure surface comprises a SAM atop the nanostructure surface and a linker layer that is reversible or irreversibly bound to the SAM.

The SAM may be any layer of organic molecule that is able to be formed on the nanostructure surface. The adsorption of the SAM onto the nanostructure may be carried out using any suitable method or chemistry known in the art. For example, in certain instances the nanostructure surface, the organic molecule of the SAM, or both are modified to promote adsorption and SAM formation.

In one embodiment, the SAM is comprised of β-cyclodextrin (β-CD), which can be adsorbed onto a nanostructure to form an ordered and densely packed SAM. The present invention is not limited to a β-CD SAM, but rather includes any SAM that may form supramolecular assemblies with a linker layer.

In certain embodiments, the nanostructure surface may be functionalized using one or more different functionalization substances that are applied or deposited onto the nanostructure surface. For example, in certain embodiments, the nanostructure surface may be modified to induce the adsorption or binding of the SAM.

Figure 14:
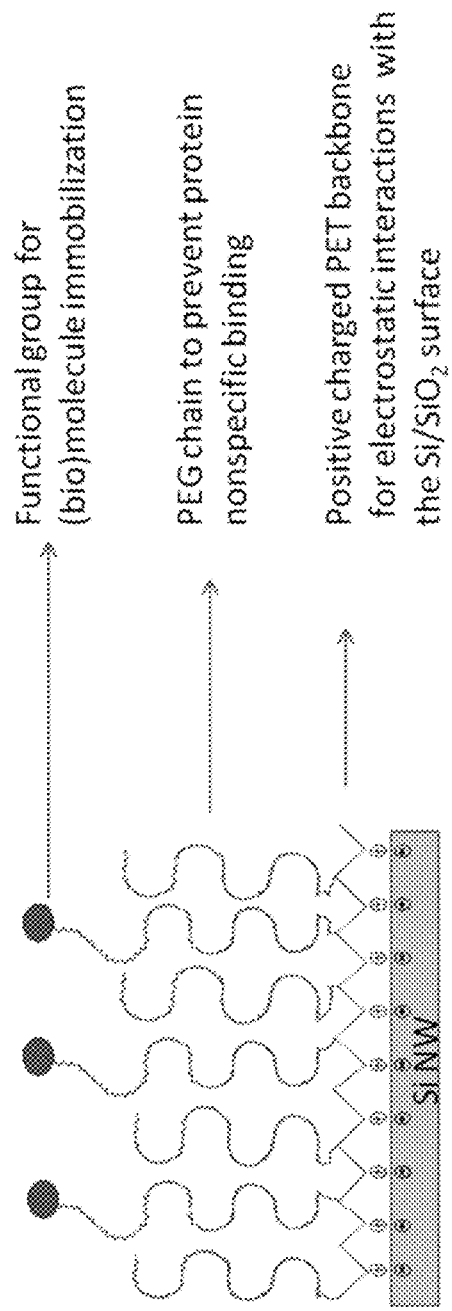
FIG. 14 is a schematic depicting an exemplary device of the invention.

In certain embodiments, and as is depicted in FIG. 14, the SAM is a polyelectrolyte thin film, which can form on a silicon or silicon dioxide nanostructure surface through electrostatic interactions. Such polyelectrolyte thin films may be selectively and controllably removed by altering the pH of the surrounding solution, which induces the desorption of the thin film thereby leaving a bare nanostructure. This alternative embodiment of regeneration of the nanosensor disrupts the functionalized coating of the nanostructure directly at the nanostructure surface, rather than at the interface between the linker layer and SAM, which is depicted in FIG. 1.

In certain embodiments, the SAM itself may be used to detect a species or analyte of interest. For example, it is described herein that β-CD SAM displays the ability to discriminate between D and L enantiomers of thyroxine.

Figure 3:
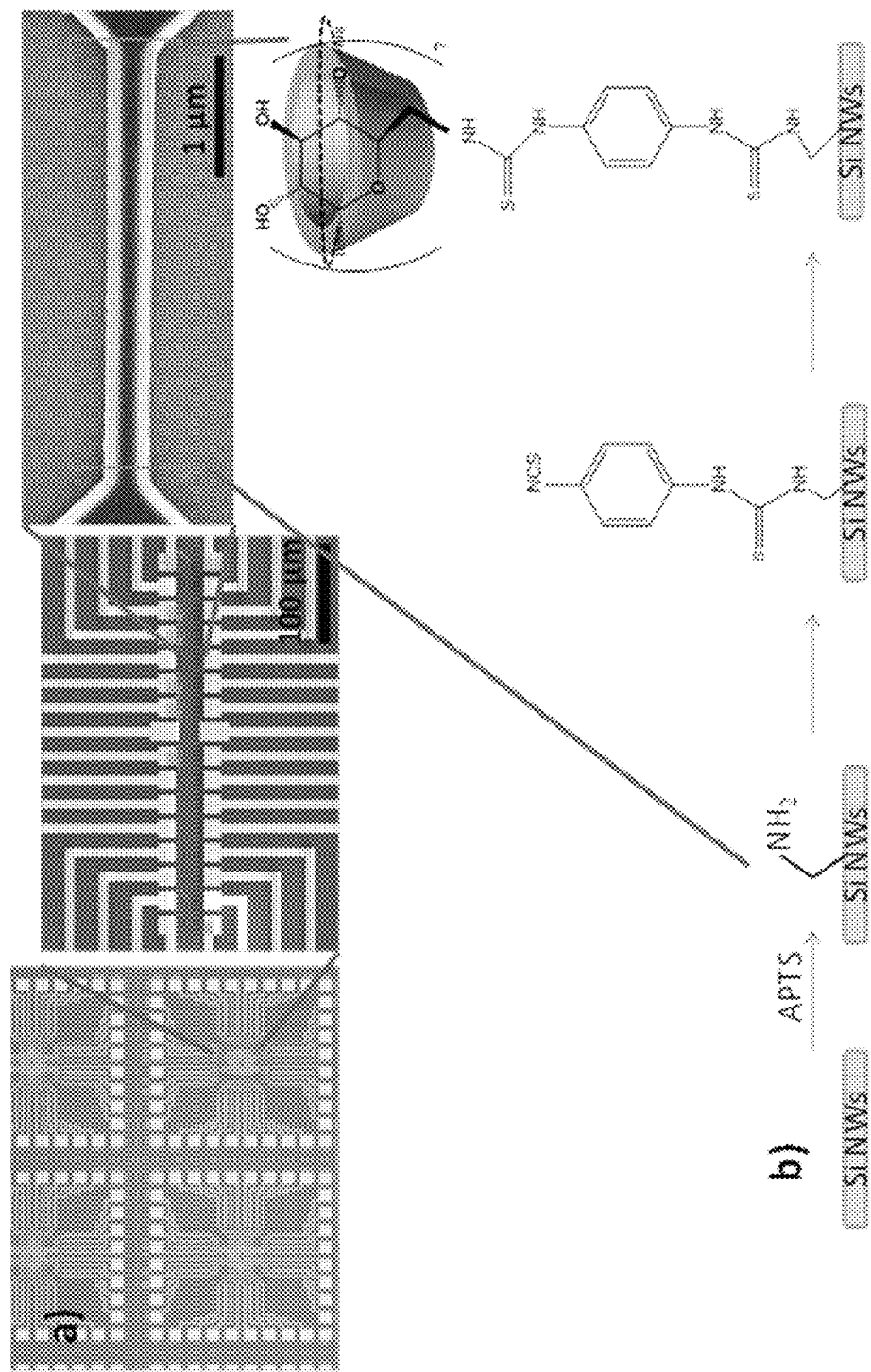
FIG. 3, comprising

In certain embodiments of the present invention, the nanostructure is functionalized in part by silanizing the nanostructure with 3-aminopropyltriethoxysilane (APTS). The nanostructure can then be subsequently reacted with p-phenylenediisothiocyanate and amino-functionalized β-CD in order to induce the formation of the β-CD SAM onto the nanostructure surface (FIG. 3B).

Dec-9-enyl carbamic acid tert-butyl ester may be used to functionalize the nanostructure because this substance has been shown to confer amine functionality. Dec-9-enyl carbamic acid tert-butyl ester may be synthesized using procedures understood by those skilled in the art. This molecule is the same as 10-N-boc-amino-dec-1-ene, which has been shown to selectively functionalize silicon-over-oxide. All chemicals required for synthesizing dec-9-enyl carbamic acid tert-butyl ester may be purchased from Sigma-Aldrich. H NMR (500 MHz, $CDCl_3$) δ 5.79 (1H, ddt, J=17, 10.2, 6.7 Hz, CH), 4.98 (1H, dd, J=17, 1.7 Hz, CH), 4.91 (1H, dd, J=10.2, 1.7 Hz, CH), 4.88 (1H, s, NH), 3.09 (2H, m, $CH_2$), 2.03 (2H, m, $CH_2$), 1.47-1.29 (12H, m, $CH_2$), 1.44 (9H, s, $CH_3$); $_{13}C$ NMR (500 MHz, $CDCl_3$) δ 156.06, 138.98, 114.20, 78.68, 40.62, 33.80, 30.12, 29.43, 29.29, 29.06, 28.92, 28.46, 26.83.

Another functionalization substance may be 2-[2-(undec-10-enyl)-4-(tetrahydro-2H-pyran-2-yloxy) phenoxy]tetrahydro-H-pyran. This molecule may be synthesized from 2-[4-(tetrahydro-2H-pyran-2-yloxy) phenoxy]tetrahydro-2H-pyran using any prior art process. The intermediate may be synthesized by first adding dihydropyran (0.83 mL, 9.1 mmol) and pyridinium p-toluenesulfonate (0.11 g, 0.45 mmol) to a solution of hydroquinone (0.25 g, 2.3 mmol) in $CH_2Cl_2$ (3 mL). This reaction mixture is then stirred for about 12 hours and diluted with 10 mL of $CH_2Cl_2$. The mixture is subsequently washed by 3×5 mL of $NaHCO_3$ and 1×5 mL brine, dried over $MgSO_4$, and concentrated to a white solid. Silica gel chromatography (4:1 hexane/ethyl acetate) provides the di-tetrahydropyran hydroquinone as a white solid (0.48 mg, 75%).

In another embodiment, nanostructure functionalization may be performed using N-hydroxysulfosuccinimide/1-ethyl-3-(3-dimethylaminoproypl) carbodiimide hydrochloride (NHS/EDC) chemistry in 1×PBS, pH 7.4.

The linker layer is a layer comprising one or more linker molecules or compounds that can be reversibly or irreversibly bound to the SAM.

Figure 5A:
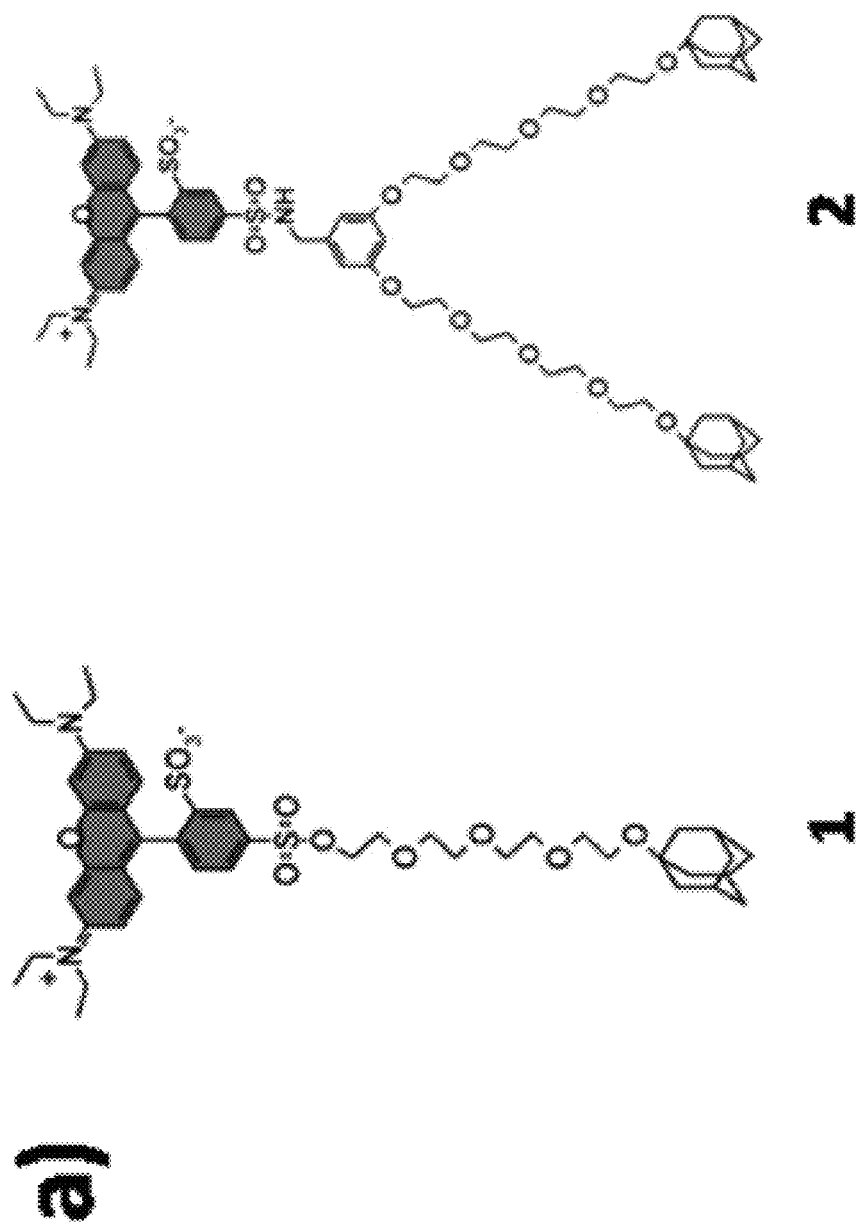
FIG. 5A through FIG. 5D, depicts the results of exemplary experiments.

In one embodiment, the linker reversibly binds to one or more molecules or compounds of the SAM. For example, in one embodiment, the linker comprises a guest moiety that reversibly binds to one or more molecules or compounds of the SAM. For example, in one embodiment, the guest moiety of the linker comprises one or more adamantane molecules, which can reversibly bind to β-CD (FIG. 5A). In one embodiment, the guest moiety is divalent, comprising two adamantane functionalities. In certain instances, the reversibility of the linkage between the linker and the SAM allows for the controllable and selective removal of the linker layer, thereby allowing for reuse of the device. For example, in certain embodiments, the binding of the guest moiety of the linker to the SAM is disrupted in order to selectively remove the linker layer from the SAM of the nanostructure.

In certain embodiments, the linker is covalently attached to the SAM. For example, in one embodiment, a linker is grafted onto a polyelectrolyte of the SAM (FIG. 14).

In certain embodiments, the linker of the linker layer comprises a chain region. For example, in certain embodiments, the linker comprises a guest moiety and a chain region extending from the guest moiety. In another embodiment, the chain region is grafted onto a polyelectrolyte thin film SAM. The chain region may comprise any suitable oligomer or polymer chain. The chain region prevents nonspecific binding of a protein or other compound to the nanostructure. In certain embodiments, the chain region comprises poly(ethylene glycol) (PEG) or oligo(ethylene glycol) (OEG) chain.

In certain embodiments, the linker comprises a receptor molecule conjugated to the chain region. The receptor molecule provides for specific binding of the analyte of interest to the coated nanostructure of the device. The receptor molecule may be any suitable small molecule, nucleic acid, peptide, protein, antibody, antibody fragment, or the like, which can specifically recognize the analyte of interest. The receptor molecule may be reversibly or irreversibly conjugated to the chain region of the linker using any suitable chemistry known in the art.

Figure 6A:
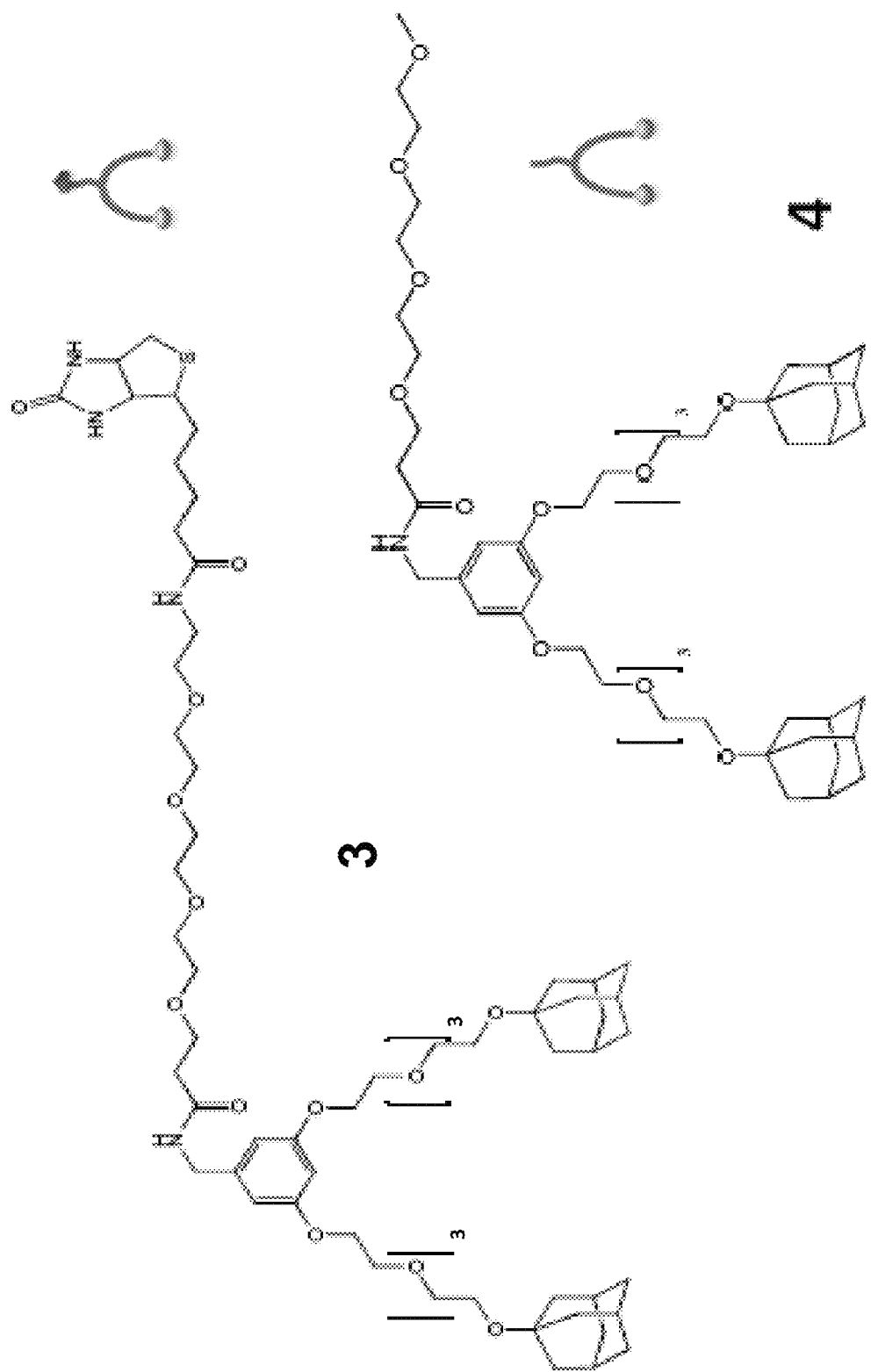
FIG. 6A and FIG. 6B, depicts the results of exemplary experiments.
Figure 6A:
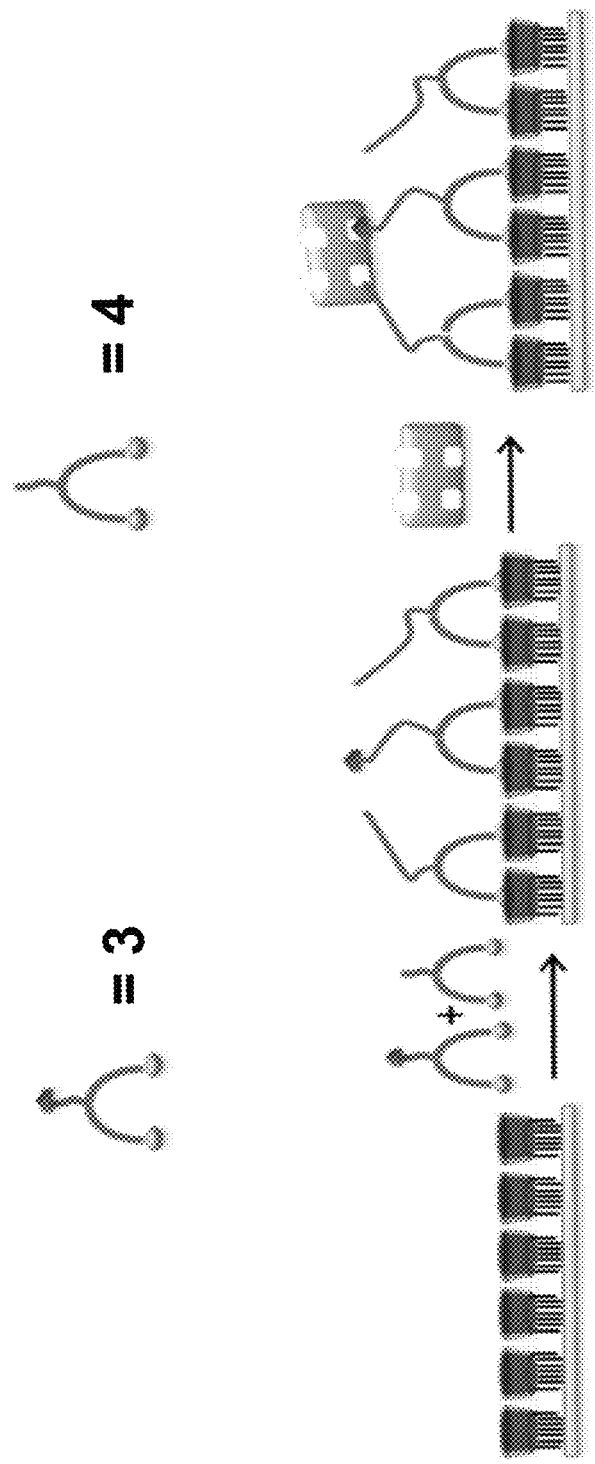

An exemplary linker comprising a biotin receptor molecule is shown in FIG. 6A as linker 3. Linker 3 comprises a divalent adamantane guest moiety, an OEG chain, and a biotin molecule as the receptor molecule. Linker 3 may be used, for example, for the detection of streptavidin, using the well-known biotin-streptavidin binding affinity.

In certain embodiments, the linker layer comprises more than one type of linker. For example, in certain embodiments, the linker layer comprises 2, 3, 4, 5, 10, 20, 50 or more different linkers. In certain embodiments, each linker comprises a distinct receptor molecule for the detection of a particular analyte of interest. Thus, the use of more than one linker allows for multiplexed detection of more than one analyte of interest.

In certain embodiments, the linker layer comprises a linker and a blocking agent. For example, as described herein, in certain instances the density of the linker in the linker layer influences the regenerative properties of the nanostructure. Therefore, in certain instances the linker layer comprises a mixture of linkers and blocking agents. In one embodiment, the blocking agent is substantially similar to the linker, except that it lacks a receptor molecule. For example, in one embodiment, the blocking agent comprises a chain region. In one embodiment, the blocking agent comprises a guest moiety.

An exemplary blocking agent comprising is shown in FIG. 6A as blocking agent 4. Blocking agent 4 comprises a divalent adamantane guest moiety, an OEG chain, but unlike linker 3 does not contain a receptor molecule. Blocking agent 4 may be used along with linker 3 to produce a linker layer which comprises a mixture of blocking agent 4 and linker 3.

The linker layer may be optimized for efficient reversibility or regeneration of the device. For example, for the detection of streptavidin using a linker comprising a biotin molecule as the receptor molecule, it was found herein that a density of ~20% of linker was optimal for regeneration of the device. However, the present invention is not limited to any particular linker density or linker to blocking agent ratio. The particular density or ratio may be dependent upon, for example, the type of SAM, type of guest moiety, type or length of chain region, and the type of receptor molecule.

The present invention includes a method for the specific detection of one or more analytes of interest present in a sample. These species or analytes can be present in solid, liquid or gaseous state in the ambient or can be applied to the device. Nanosensor devices of the present invention, and their associated methods of use, may be used in diagnostic applications, industrial applications, and the like. For example, in certain embodiments the method of the invention comprises detecting the presence or amount of one or more analytes of interest in a fluid sample. The fluid sample may be, for example a physiological solution, including, but not limited to, blood, serum, urine, bile, sweat, and the like. In certain embodiments, the fluid sample is derived from a biological sample. For example, the fluid sample may be a suitable buffer or solution comprising a biological sample, including but not limited to a cell, cell extract, tissue, and the like.

The device and method of the present invention, for example, are especially suited for detecting, measuring, or both, of proteins, DNA, small molecules and intrinsic cellular changes or cellular changes due to extrinsic stimuli. Still further, sensors, as described and provided herein, may also be suitable for sensing cellular interactions due to paracrine, autocrine, or endocrine signaling, or combinations thereof.

In certain embodiments, the method comprises the use of the reversibly functionalized device described herein for the detection of one or more biomarkers, which may indicate the presence of a disease, severity of a disease, risk for developing a disease, optimal treatment, treatment efficacy, and the like.

Functionalized nanosensor devices may be used to detect certain macromolecules based on selective protein binding. For example, nanosensor devices of the present invention can be used to detect protein biomarkers in a sample. In the detection of biomarkers, the nanostructure surface is functionalized with linkers comprising a receptor molecule that specifically bind to the biomarker. For example, receptor molecules can include antibodies, antibody fragments, binding proteins, receptors, nucleotide sequences, and the like. In one example, nanostructure surfaces are functionalized with antibodies that specifically bind prostate-specific antigen (PSA) to allow the detection of PSA in a sample. In another example, nanostructure surfaces of CA15.3 in a sample. PSA and CA15.3 are both biomarkers associated with cancer. Other cancer biomarkers include, but are not limited to CA27.29, CEA, CA125, CA19.9, AFP, b-hCG, HER-2, KRAS, IL-6, IL-8, TRAIL, VEGF, TNF alpha, TGF alpha, Leptin, Prolactin, and the like. As would be understood by those skilled in the art, the type of biomarker detected by exemplary nanosensors of the present invention is not limited. Rather, any biomarker, in which a biomarker-specific receptor molecule can be functionalized to the nanostructure surface, can be detected.

Functionalized sensor devices may also be utilized in the detection of a nucleic acid or portion thereof, including, but not limited to DNA and RNA. For example, in certain embodiments, the receptor molecule may be a polynucleotide, peptide, protein, antibody, antibody fragment or the like. In one embodiment, the receptor molecule is a polynucleotide probe comprising a sequence that is complementary to the nucleic acid sequence of interest. For example, the polynucleotide probe may be used to detect the presence of a particular mutant or variant nucleic acid sequence.

In one embodiment, the sensor devices of the invention are used for the discrimination between enantiomers. For example, it is described herein that the β-CD SAM displayed the ability to selectively discriminate between the D and L enantiomers of thyroxine.

According to another embodiment, functionalized nanosensor devices are capable of reversing sensor responses to the addition or removal of reagents. For example, sensor responses may be reversed upon washing out of a fluid sample from the solution chamber.

The present invention includes a method of manufacturing a regenerative nanosensor device. In one embodiment, the method comprises coating the nanostructure of a sensor device with a reversible functionalized coating. As described elsewhere herein, the present invention is not limited to any particular nanostructure. Rather, the method comprises forming a reversible functionalized coating onto any suitable nanostructure, including, but not limited to, a nanowire, nanoribbon, nanotube, carbon nanotube, extended gate field effect transistor and the like. In one embodiment, the method comprises forming a SAM atop the nanostructure surface. In one embodiment, the method comprises contacting the nanostructure with a molecule or compound which forms a SAM. For example, in one embodiment, the method comprises contacting the nanostructure with β-CD in order to form a β-CD SAM. In one embodiment, the method comprises applying a solution comprising β-CD to the nanostructure surface thereby inducing the adsorption of β-CD to the surface.

In one embodiment, the method comprises forming a linker layer atop the SAM. In one embodiment, the method comprises contacting the SAM to a linker, which has a guest moiety that reversibly binds to the SAM. For example, in one embodiment, the method comprises contacting a β-CD SAM with a linker comprising adamantane, where the adamantane reversibly binds to the β-CD. As described elsewhere herein, the linker is conjugated to a receptor molecule, thereby providing the functionalized supramolecular assembly coated onto the nanostructure.

In one embodiment, the method comprises forming a SAM comprising a polyelectrolyte thin film, which may electrostatically bind to the nanostructure surface. In one embodiment, the molecule or compound forming the SAM is prebound to a linker. For example, in certain embodiments, the linker is grafted onto the molecule or compound forming the SAM.

The present invention also includes a method of reusing a regenerative nanosensor device by replacing the receptor molecule functionalized on the nanostructure surface. As described herein, the nanosensor device of the present invention comprises a nanostructure having a reversible functionalized coating, wherein one or more layers of the coating may be controllably and selectively removed without damage to the underlying nanostructure. This allows the device to be reused over time, without any impairment to device performance. Further, the regenerative nanosensor devices allows for the device to be calibrated only a single time, which can then be reused for multiple sensing applications.

In one embodiment, the method of replacing the receptor molecule of the regenerative device comprises disrupting the supramolecular assembly of the coating to controllably remove at least one layer of the functionalized coating, thereby removing the receptor molecule. In certain embodiments, removal of at least one layer of the functionalized coating comprises applying a solution or buffer to the nanostructure that induces the removal or desorption of the at least one layer. In one embodiment, applying a solution to the solution chamber which competes with the SAM for binding to the guest moiety of the linker induces the linker to dissociate from the SAM. For example, in one embodiment, the method comprises applying to the solution chamber a solution comprising β-CD. The solution β-CD competes with the β-CD SAM for the binding of the adamantane guest moiety of the linker, thereby causing the desorption of the linker layer leaving the β-CD SAM atop the nanostructure surface. In another embodiment, applying to the solution chamber a solution having an altered pH can induce the removal of a polyelectrolyte thin film from the nanostructure surface, thereby leaving the bare surface.

In certain embodiments, the method comprises the re-adsorption of the one or more layers that had been selectively removed. For example, the nanostructure surface can be subjected to subsequent adsorption of a SAM, linker layer, or both to provide a new functionalized coating to the nanostructure. In one embodiment, the nanostructure may be functionalized for reuse for detection of the same analyte of interest. In another embodiment, the nanostructure may be functionalized for use for the detection of a different analyte of interest.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Regenerative Electronic Biosensors Using Supramolecular Approaches

Presented herein is the development of a supramolecular interface for Si nanowire FETs, which can be used in creating regenerative electronic biosensors (Duan et al., 2013, ACS Nano, 7(5): 4014-4021). The key to the approach is Si-NWs functionalized with β-cyclodextrin (β-CD), to which receptor moieties can be attached with an orthogonal supramolecular linker. Full recycling is demonstrated herein using the strongest biomolecular system known, streptavidin (SAv)-biotin. The bound SAv and the linkers can be selectively removed from the surface through competitive desorption with concentrated β-CD, regenerating the sensor for repeated use. An added advantage of β-CD is the possibility of stereoselective sensors, and the ability to quantify the enantiomeric composition of chiral targets is demonstrated herein.

Supramolecular interactions have been of interest as an alternative strategy for (bio)molecule attachment on different surfaces due to its high specificity, controllable affinity, and reversibility (Mulder et al., 2004, Org. Biomol. Chem., 2: 3409-3424; Elemans et al., 2009, Angew. Chem., Int. Ed., 48: 7298-7332; Ludden et al., 2006, Chem. Soc. Rev., 35: 1122-1134). Among all the potential candidates, β-cyclodextrin (β-CD)-based host-guest chemistry is particular attractive, since CD molecules are able to form densely packed self-assembled monolayers (SAMs) that can complex with a variety of hydrophobic organic molecules with different binding affinities (Ludden et al., 2006, Chem. Soc. Rev., 35: 1122-1134; Huskens et al., 2002, Angew. Chem., Int. Ed., 41: 4467-4471; Davis et al., 2004, Nat. Rev. Drug Discovery, 3: 1023-1035; Houk et al., 2003, Angew. Chem., Int. Ed., 42: 4872-4897; Chen et al., 2010, Chem. Soc. Rev., 39: 495-505). Recently, the selective attachment of proteins to β-CD SAMs through multivalent orthogonal interactions has been reported (Ludden et al., 2006, Small, 2: 1192-1202; Ludden et al., 2007, Angew. Chem., Int. Ed., 46: 4104-4107).

The data presented herein utilizes the CD strategy—specifically, functionalizing a Si NWFET with β-CD SAMs—to detect small hormone molecules and proteins. Such supramolecular interfaces have the advantages of controlled attachment of (bio)molecules to the NWFET surface with respect to kinetics, thermodynamics, and orientation. In addition to homogeneous and oriented attachment, the CD strategy allows the regeneration of the nanowire surface and reuse of the functionalized devices.

The materials and methods employed in the experiments are now described.

Materials

3-Aminopropyltriethoxysilane (APTS), p-phenylene diisothiocyanate (PDC), and 4-(2-hydroxyethyl)-1-piperazineethanesulfonic acid (HEPES) were purchased from Aldrich. d-Thyroxine and 1-thyroxine were ordered from MP Biomedicals LLC. EZ-Link NHS-PEG$_4$-biotin, and EZ-Link NHS-PEG$_4$ were purchased from Fisher Scientific Company LLC. All materials were used as received without further purification. Streptavidin-unconjugated was purchased from Rockland Immunochemical. The lyophilized streptavidin was restored with deionized water and diluted to the desired concentrations with buffers before using. Per-6-amino-(3-cyclodextrin, lissamine-Ad (1), lissamine-Ad$_2$ (2), and amino-terminated divalent adamantyl linker were synthesized at the lab of one of the authors (J. H.) according to previously published results (Chen et al., 2010, Chem. Soc. Rev., 39: 495-505; Ashton et al., 1996, J. Org. Chem., 61: 903-908).

Divalent Biotin Linker and PEG Blocking Agents (3, 4)

Figure 8:
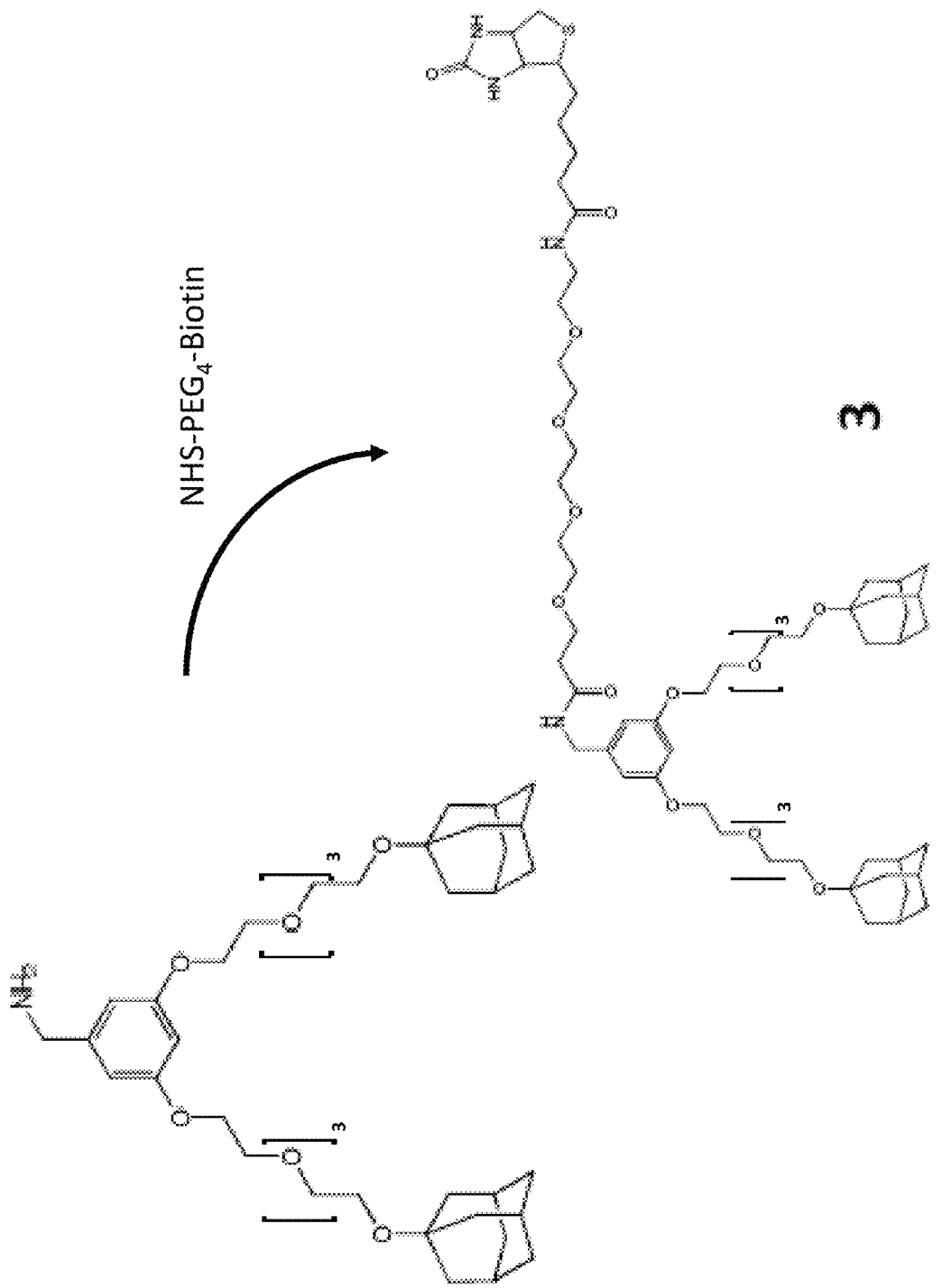
FIG. 8 depict the synthesis routes towards the divalent linkers 3 and the blocking agent 4.
Figure 8:
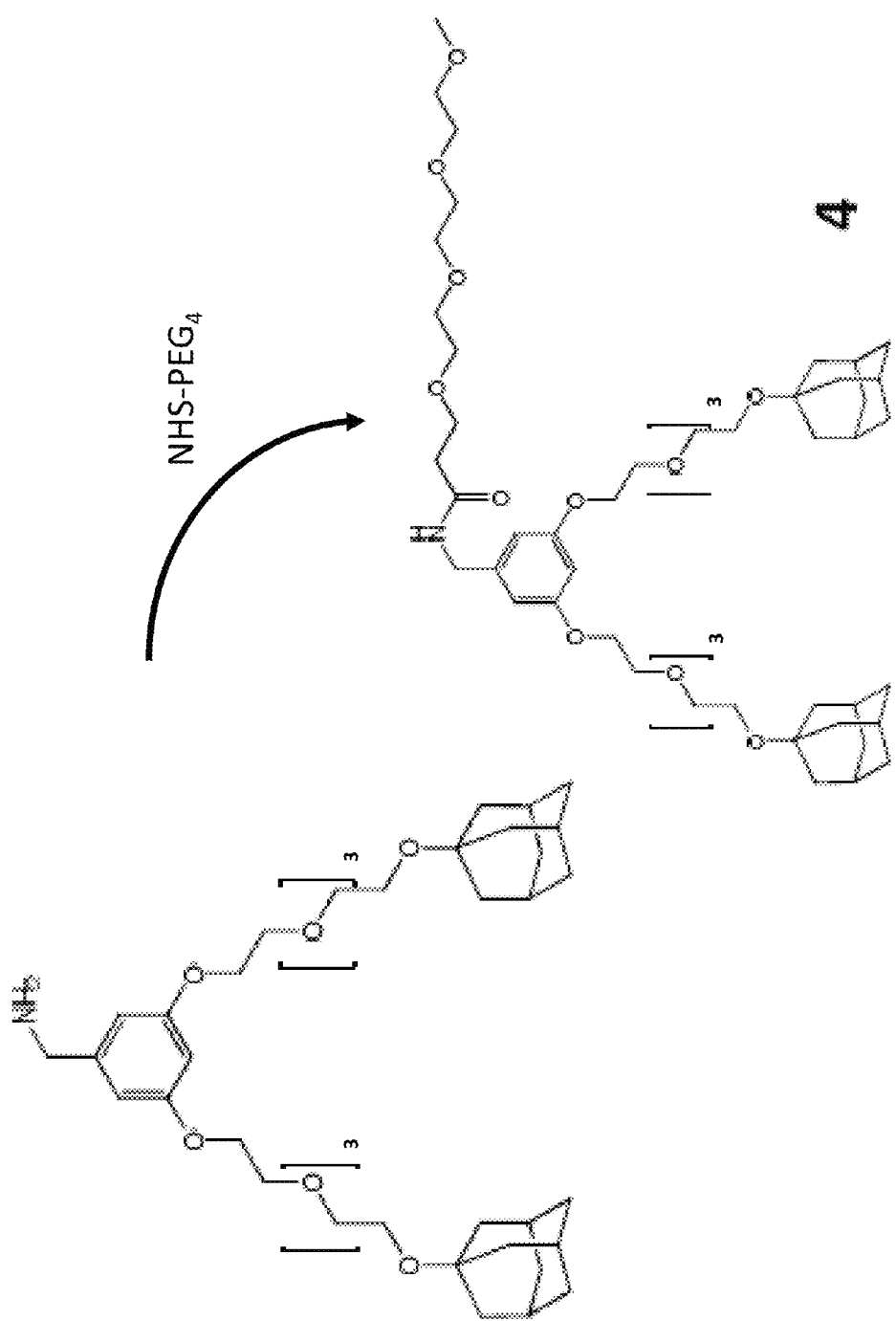

These were prepared by mixing amino-terminated divalent adamantyl linker with EZ-Link NHS-PEG$_4$-biotin or EZ-Link NHS-PEG$_4$ in DMF (1:3) (FIG. 8). The mixture was stirred at room temperature for 3 h. Subsequently, diethyl ether was added dropwise, and the product precipitated. The product was redissolved in DMF and precipitated again by adding diethyl ether dropwise.

Si Nanowire FET Biosensor Fabrications

The devices were fabricated from 4-inch SOI wafers (Soitec). The silicon active layer (p-type doping=$10^{15}$ cm$^{-3}$) was first thinned to about 45 nm by thermal oxidation, and the silicon oxide removed using wet etching (BOE Etch). The source and drain regions as well as the back-gate were patterned by contact lithography and doped by $BF_2^+$ implantation. Following dopant activation in a furnace at 1000° C., the NW channels were patterned in hydrogen silsesquioxane by electron beam lithography, and for the nanoribbon devices, the 1 µm wide mesas were defined by optical lithography. The pattern was transferred through the active silicon layer using either a TMAH anisotropic wet etch (25% in $H_2O$ at 50° C.), a $Cl_2$ inductively coupled plasma etch (Oxford 100), or a $CF_4$ reactive-ion etch (Oxford 80). The devices were then metalized by titanium/gold evaporation and patterned by lift-off. The metal contacts were annealed in a rapid thermal processor at 450° C. for 1 min, and devices were measured to ensure the presence of ohmic contacts. The final step was to passivate the devices with a 1 µm layer of SU8 photoresist with lithographically patterned openings at the top of the devices, the contact pads. The wafer was then hard-baked at 130° C. for 20 min.

Device Functionalization

The Si-NW oxide surfaces were cleaned with UV ozone (UV/Ozone ProCleaner Plus, Bioforce Nanosciences) for 5 min before functionalization. Then APTS was allowed to evaporate onto the $SiO_2$ surface through gas phase deposition for 5 h. The devices were then baked in a vacuum oven for 30 min at 120° C. Transformation of the amino-terminated layer to an isothiocyanate-bearing layer was accomplished by exposure to a 0.01 M solution of PDC in ethanol at 40° C. for 1 h, followed by rinsing with copious amounts of ethanol and drying in a stream of nitrogen. The surface-confined β-CD layer was obtained by immersion of the isothiocyanate-covered Si-NWs in a 5 mM aqueous solution of per-6-amino-β-cyclodextrin at 40° C. for 1 h. After reaction, the samples were washed with Millipore water for 5 min and rinsed with additional water to remove physisorbed material and dried in a stream of nitrogen. The rather stable CD molecules allow for the long-term storage of the functionalized sensors. For example, the same CD-modified chip has been used for more than half a year, without any observations of degradations of the chemical surface, whereas unprotected amine-modified chips typically last only 1 week.

Fluid Delivery System

The mixing cells (solution chamber) were created by epoxying thin-walled, ~5 mm diameter PTFE tubing to the chip surface. Microminiature reference electrodes (Harvard Apparatus) and thinner tubing (0.5 mm) serving as the fluid supply and return were inserted. The solution input tube was placed directly over the central region of the die. This system enabled continual mixing (equivalent to pipetting up and down) throughout the course of sensing measurements. In the sensing setup, different samples were pumped by a single syringe pump, and the sample exchange was achieved by using an electronically controlled solenoid valve (typical switching speed of within a second), thus maintaining a constant flow rate (100µ/min). In these conditions, no change in sensor response was observed by switching the samples.

The results of the experiments are now described.

Figure 11:
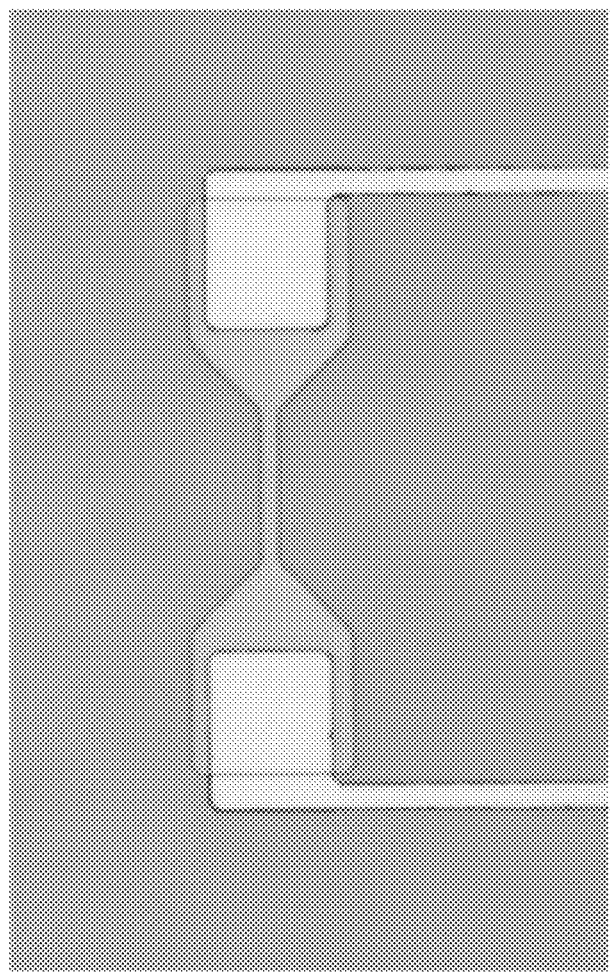
FIG. 11 is an optical image of a single Si nanoribbon type FET device. The purple layer is the Si nanoribbon mesa, on top of the green SiO2 BOX (buried oxide layer). The yellow regions are metal interconnects.

Si NWFETs were fabricated from SOI wafers (Soitec) with 45 nm of boron-doped active Si layer in a lithography process similar to the ones previously described (Rajan et al., 2010, IEEE Electron Device Lett., 31: 615-617). The nanowires used for the experiments are 150 nm (FIG. 3A) or 1 µm wide (silicon nanoribbon type, FIG. 11) and have a variable length from 1.5 to 10 µm long. The devices were covered with a passivation layer of SU-8 (an epoxy-based negative photoresist) with windows opened for the NW channel and the contact pads.

Figure 9:
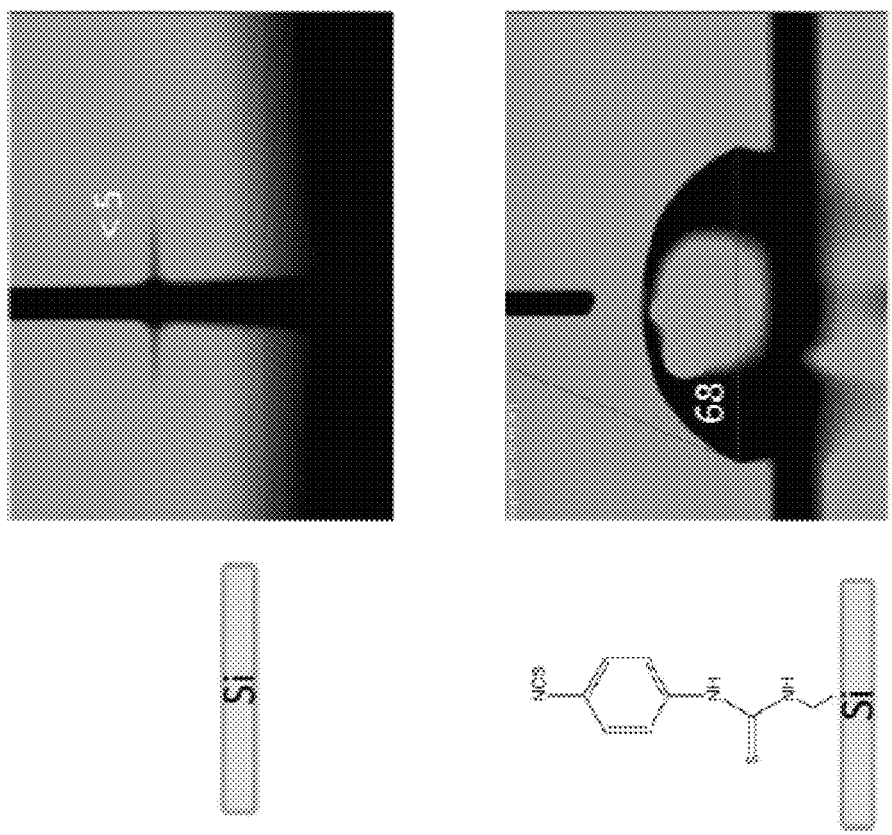
FIG. 9 depicts the results of exemplary experiments demonstrating the water contact angle measurements of β-CD functionalized Si wafer.
Figure 9:
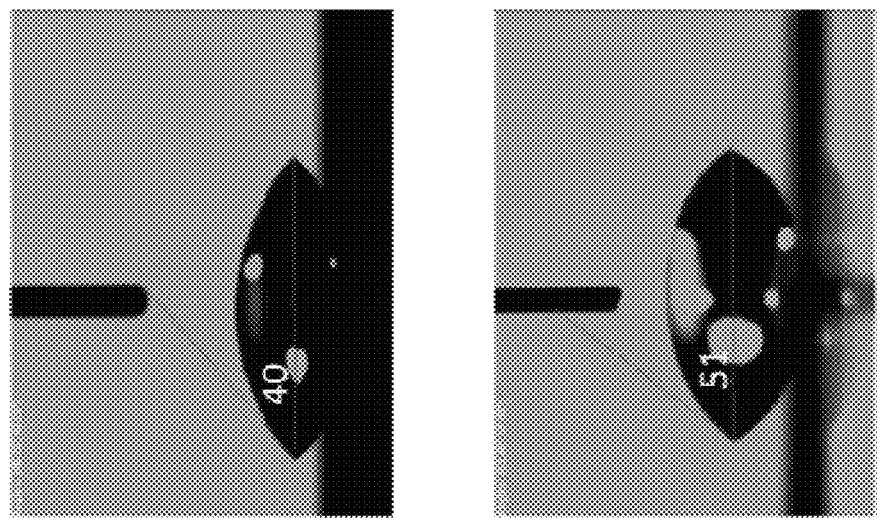
Figure 9:
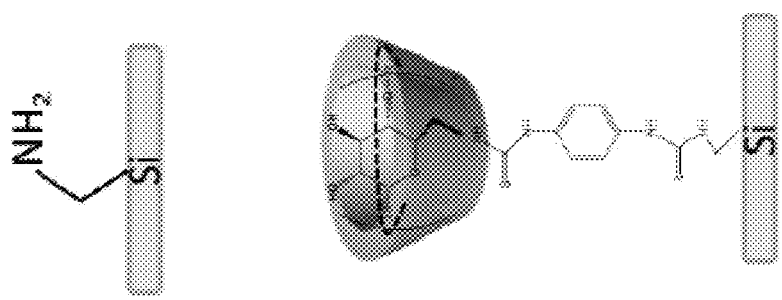
Figure 10A:
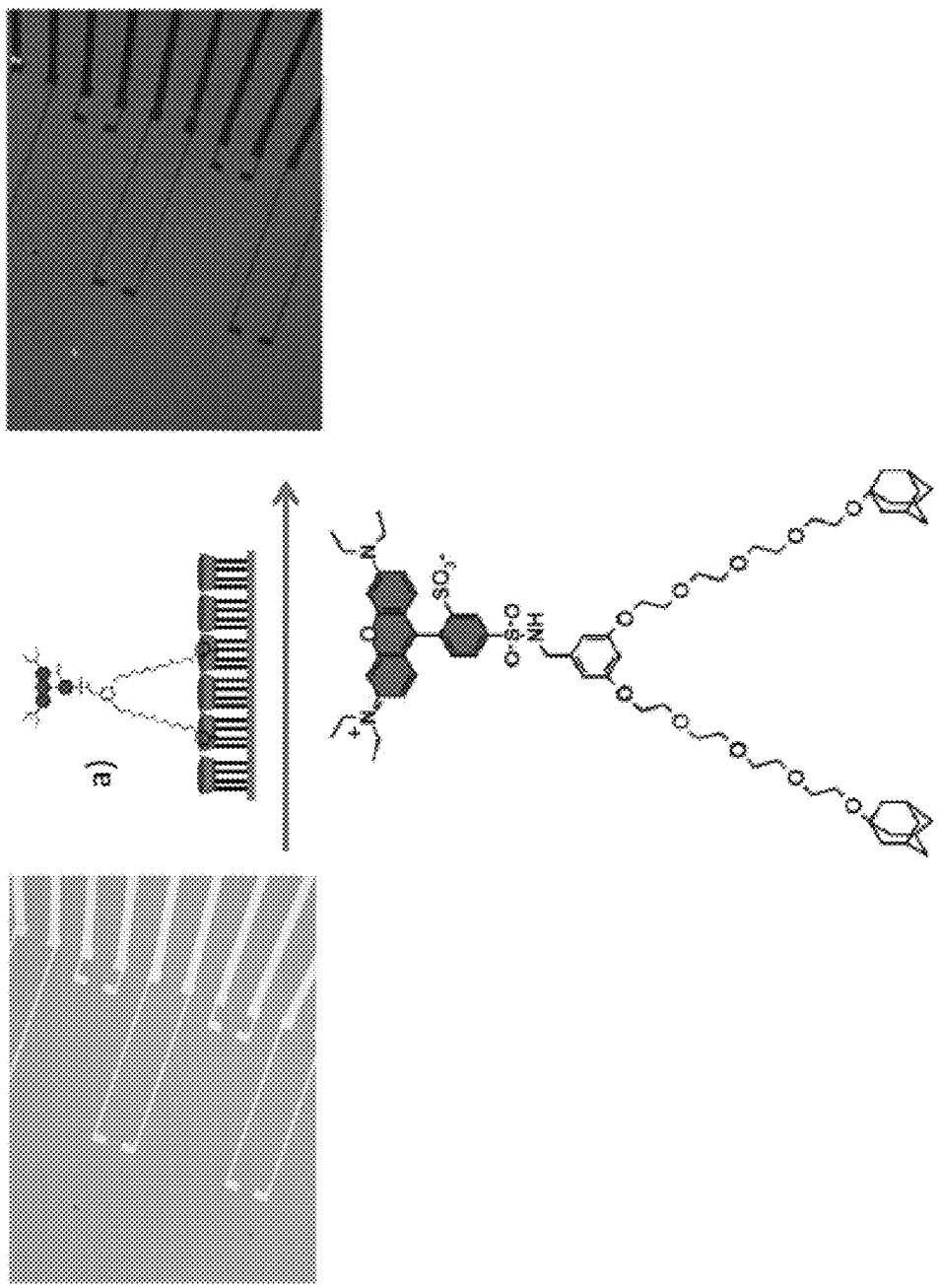
FIG. 10A through FIG. 10C, depicts the results of exemplary experiments demonstrating fluorescent images of divalent fluorescently labeled guest molecule absorption (FIG. 10A) and desorption (FIG. 10B) on β-CD functionalized Au—Si patterned substrates.
Figure 10B:
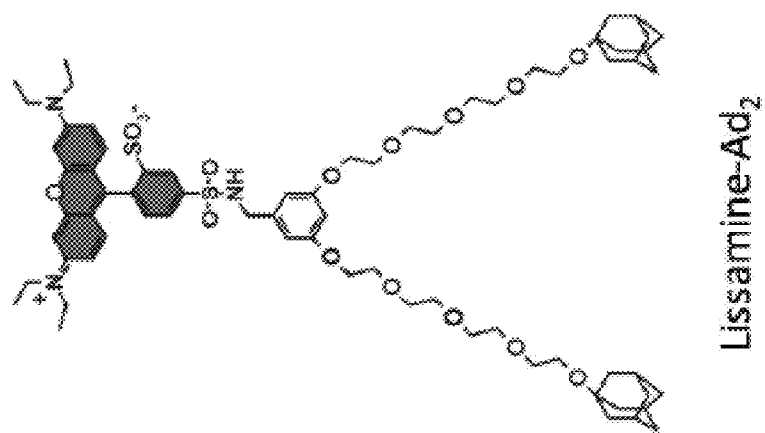
Figure 10B:
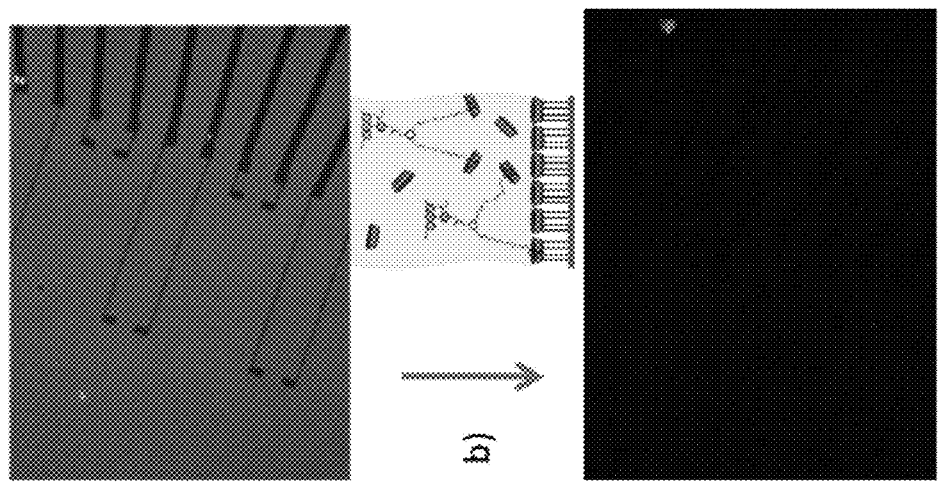
Figure 10C:
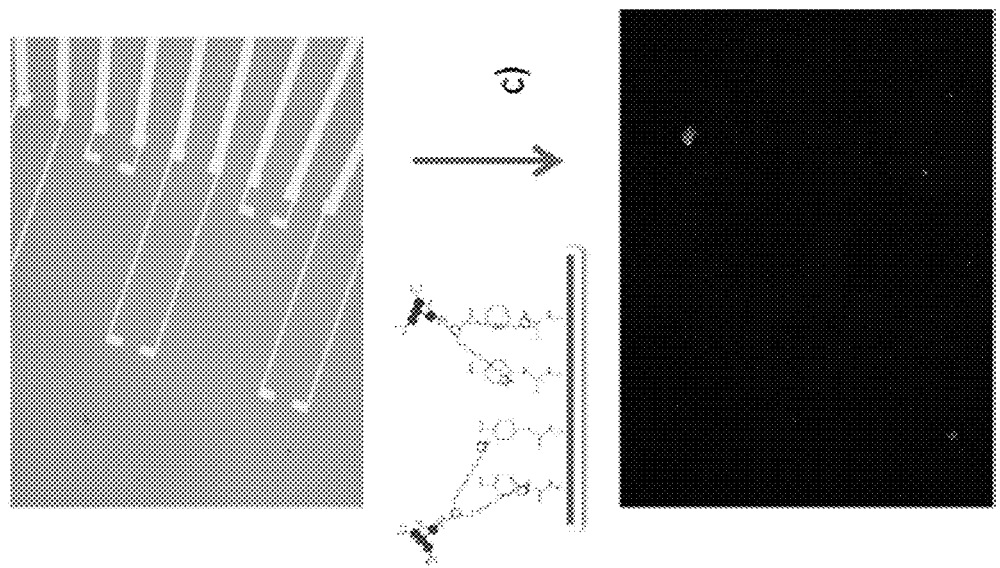
Figure 10C:
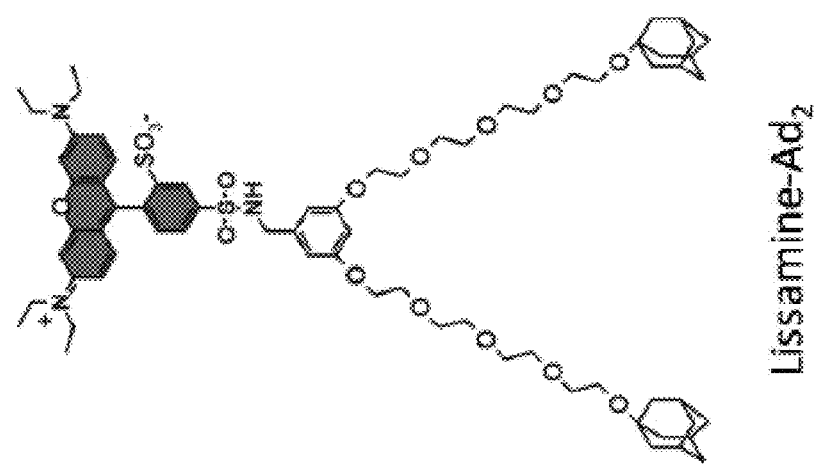

The Si NWFETs were functionalized with β-CD using a three-step procedure that is adapted from a similar procedure to prepare β-CD monolayers on silicon (FIG. 3B) (Onclin et al., 2004, Langmuir, 20: 5460-5466; Mulder et al., 2005, Small, 1: 242-253). First the NW surface was silanized with 3-aminopropyltriethoxysilane (APTS) through the gas phase. Subsequently, the NW was reacted with p-phenylenediisothiocyanate and amino-functionalized β-CD to give a β-CD monolayer (FIG. 3B). Because of Debye screening, (Steprn et al., 2007, Nano Lett. 2007, 7, 3405-3409) a short aminosilane (APTS) was used to ensure the functionalized β-CD monolayer is close to the NW surface, to maximize the sensitivity of the NWFETs. The functionalization scheme was validated by fluorescence, ellipsometry, and water contact angle goniometry. After CD functionalization, a fluid delivery system consisting of a plastic solution chamber (mixing cell) together with a microminiature reference electrode (Harvard Apparatus) was mounted on top of bonded dies containing the Si NWFET devices. Continuous flow was used during sensing measurement (typical flow speed, 100 µL/min). These conditions ensure the fast mixing of the analytes and a stable solution gating during the sensing experiments (FIG. 9).

The CD functionalization scheme was first validated on planar silicon substrates. The surface reactions were monitored with water contact angle goniometry (FIG. 9) and ellipsometry (Table 1). A clear change in the polarity of the surface was observed after the isothiocyanate derivatization of the amino layer, which is observed by an increase in the water contact angle from 40° to 68°. Ellipsometry (performed on isothiocyanate monolayers on silicon) showed no significant thickness increase. Reaction of the isothiocyanate-terminated layer with amino functionalized β-CD to give the surface-confined host layer on silicon was accompanied by an increase in the ellipsometric thickness to 0.8 nm, which is in good agreement with the dimension of the β-CD molecules. A decrease in the contact angle was also observed. All the results are consistent with earlier observations (Onclin et al., 2004, Langmuir, 20: 5460-5466).

To further prove the CD functionalization, micro gold-silicon patterns were fabricated to facilitate the evaluation of the chemical functionalization by fluorescence microscopy. After CD functionalization on Au—Si substrates, a fluorescently labeled guest molecule bearing two adamantyl (Ad) units was complexed with the CD layer. Clear fluorescent patterns were observed by fluorescence microscopy (FIG. 10). The patterns are rather stable with aqueous rinsing but could be selectively removed by the competitive desorption with high concentrations of β-CD solution (8 mM). As a control experiment, PITC functionalized Au—Si substrates did not exhibit fluorescence patterns after incubating with the same fluorescent dyes. These results indicate that multivalent, specific interactions between the fluorescent Ad guest molecules and the CD monolayer are responsible for the observed fluorescent patterns which proved the successful CD functionalization on silicon surfaces. The same chemical functionalization scheme was applied on the Si nanowire sensors under the same conditions.

TABLE 1

Static water contact angles (Θ) and ellipsometric thickness on flat silicon substrates

| Terminal functionality | Θ (°) | Ellipsometric thickness (nm) |
|---|---|---|
| Silicon | <10 | — |
| —NH$_2$ | 40 ± 5 | 0.9 ± 0.5 |
| —SCN | 68 ± 3 | 0.9 ± 0.4 |
| β-CD | 51 ± 3 | 1.7 ± 0.5 |

Figure 4A:
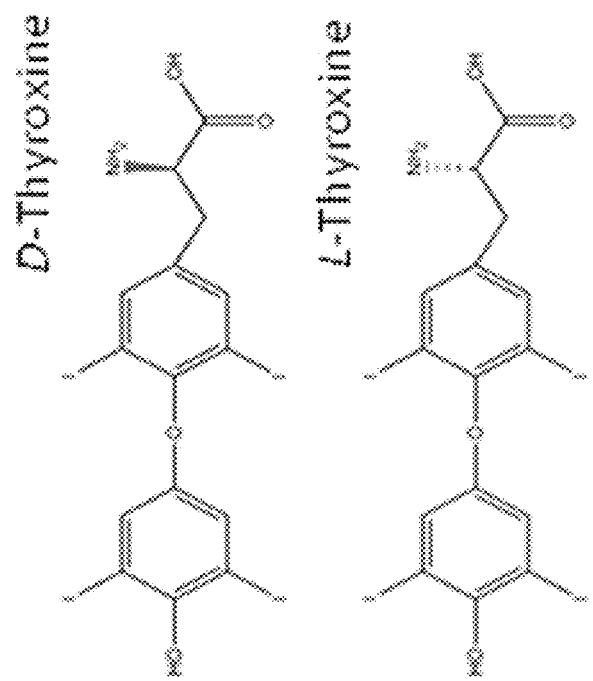
FIG. 4A through FIG. 4D, depicts the results of exemplary experiments.
Figure 4A:
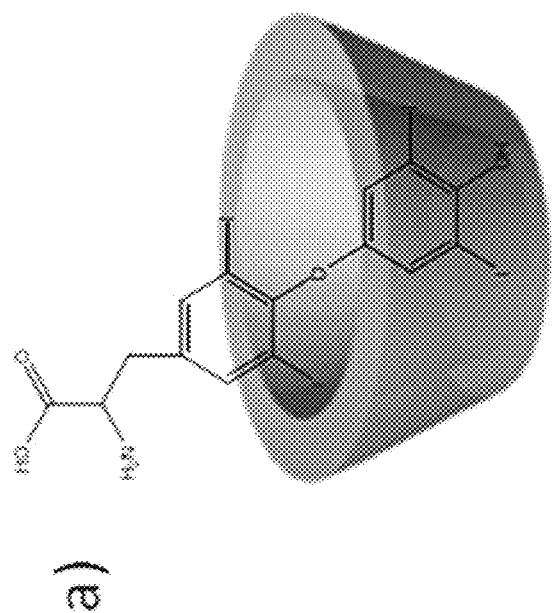

To demonstrate the recognition and reversibility of the CD functionalization, the β-CD-functionalized Si NWFETs were first used to detect thyroxine enantiomers (FIG. 4A). It is known that the biological activity of many compounds depends on their chirality, so that it is of great importance to know which compound enantiomer is present and to precisely determine the respective enantiomeric purity (e.g., enantiomeric composition) (Maier et al., 2001, J. Chromatogr. A, 906: 3-33). The two enantiomers of thyroxine (3,5,3',5'-tetraiodothyronine) are d-thyroxine and l-thyroxine (often abbreviated as T4), the main thyroid gland hormone. Synthetically prepared l-thyroxine is used in the treatment of thyroid gland deficiency diseases; however, its counterpart d-thyroxine cannot be used for medical purposes due to cardiac side-effects (Oppenheimer et al., 1987, Endocr. Rev., 8: 288-308). Successful chiral analysis often requires a receptor molecule that can form a more stable diastereomeric complex with one of the enantiomers, and β-CDs have shown enantioselectivity in their interactions with chiral guests both in solution and on surfaces (Easton et al., 1996, Chem. Soc. Rev., 25: 163-170; Shahgaldian et al, 2005, J. Inclusion Phenom. Macrocyclic Chem., 53: 35-39; Szejtli, 1998, Chem. Rev., 98: 1743-1753; Kurzawski, 2009, Anal. Chem., 81: 9353-9364; Kieser et al., 2002, Anal. Chem., 74: 3005-3012).

Figure 4B:
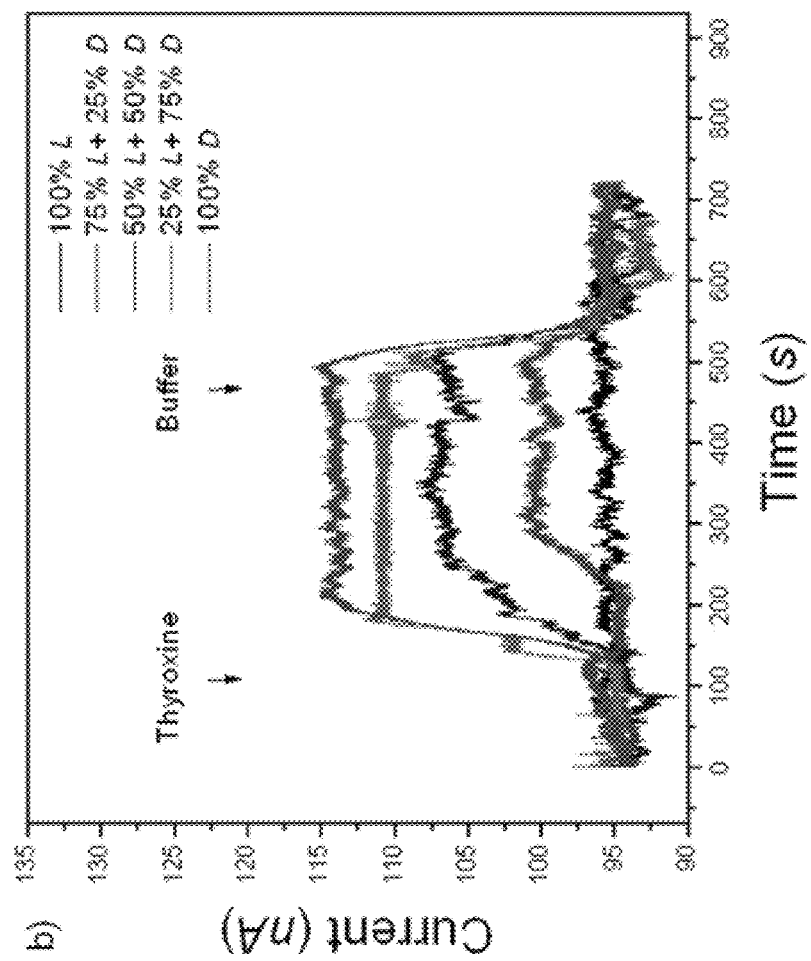

Here it is demonstrated that β-CD-functionalized Si NWFETs are able to discriminate between the enantiomers of thyroxine. d- and l-thyroxine solutions (1 nM) were prepared in sodium carbonate buffer (pH 10.5, 1 mM), and variable concentration ratios of the enantiomers were prepared by mixing these solutions. FIG. 4B presents binding and unbinding sensograms obtained for different compositions of d- and l-thyroxine utilizing the same device. After a stable baseline was established, a solution of thyroxine was injected, and a clear increase of measured current is observed, which agrees with the negative charge of thyroxine at pH 10.5. After sensor equilibrium, the thyroxine solution was replaced by buffer and the complex was allowed to dissociate. During the experiment a return to a stable baseline was obtained, indicating the thyroxine-CD interactions are reversible and no degradation of the CD-SAM on the Si NWFETs occurs. It is also observed that the sensor responses increased with increasing percentage of the d-enantiomer, demonstrating a differential selective binding of the d- over the l-enantiomer of thyroxine on the CD-functionalized Si-NW sensor. Since the CD-thyroxine interactions are totally reversible and the sensors can be used multiple times, a "calibration curve" can be established for each chip, which means that the CD-functionalized Si-NWs can be used for the evaluation of the enantiomeric composition of a racemic mixture of d- and l-thyroxine. It is believed that this is the first time that a Si NWFET was demonstrated as a chiral sensor to quantify the enantiomeric compositions. While not wishing to be bound by any particular theory, it is expected that Si NWFETs can be extended to other chiral systems, suggesting that this approach could serve as a technology platform to improve drug discovery and development. Compared with other state of the art surface based biosensors such as surface plasmon resonance (SPR) and quartz crystal microbalance (QCM), the Si NWFET detects changes in surface charge density by binding of charged molecules, which has advantages over refractive index or mass detection, which is limited by the molecule weight of the analytes (typically required above 2000 g/mol when covering the surface in a monolayer fashion (Myszka, 1997, Curr. Opin. Biotechnol., 8: 50-57)).

Figures 4C, 4D:
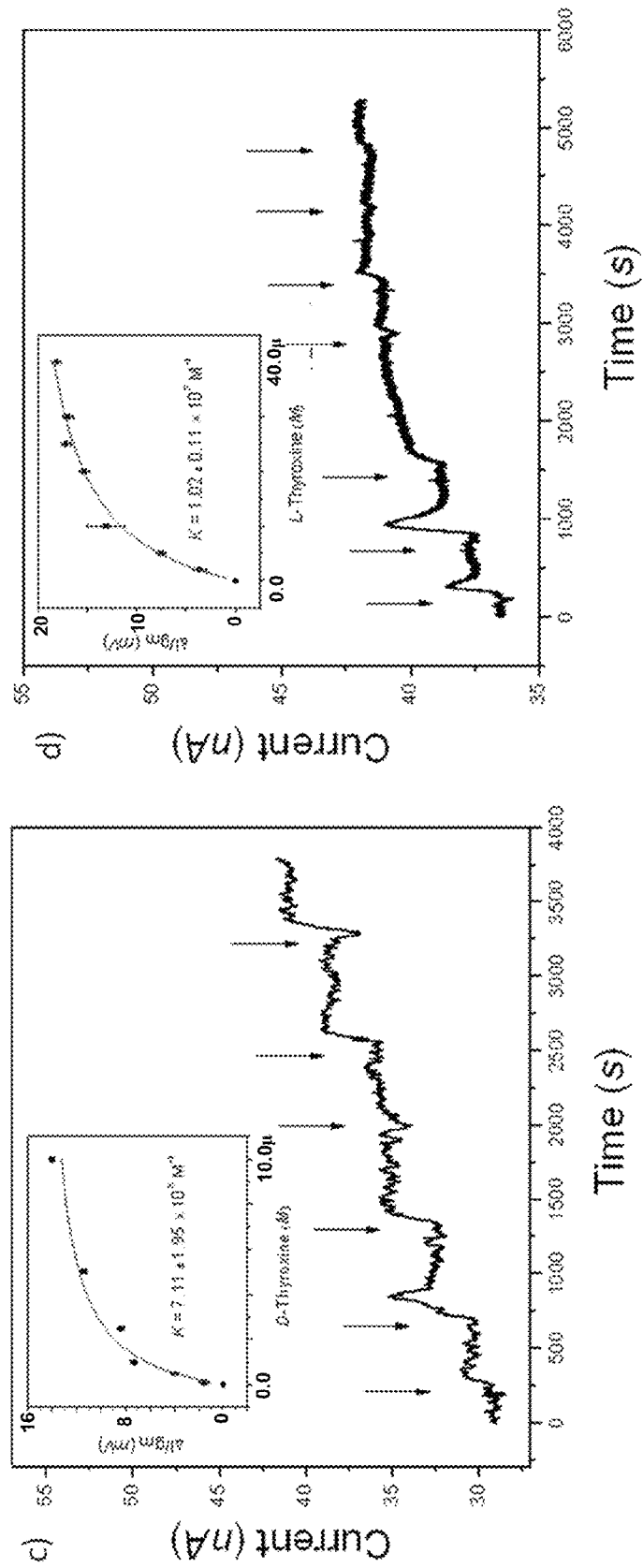

Furthermore, in order to quantify the inclusion complexation behavior of the CD SAMs with the thyroxine guests, surface titration experiments (FIG. 4C-FIG. 4D) were performed with CD-functionalized Si-nanoribbon-type devices with different concentrations of d- and l-thyroxine under the same buffer conditions. FIG. 4C shows the real-time sensor responses by adding increasing concentrations of d-thyroxine. After the baseline was established, d-thyroxine solutions with concentrations of 0.1, 0.5, 1, 2.5, 5, and 10 nM (indicated by arrows in FIG. 4C) were sequentially injected into the flow channel, which resulted in an increase of current owing to higher equilibrium surface coverage. The measured current change of the nanowire sensor (ΔI) was calibrated using $\Delta I/g_m$ to obtain the surface potential change (Ishikawa et al, 2009, ACS Nano, 3: 3969-3976; Vacic et al., 2011, Biosens. Bioelectron., 28: 239-242), which corresponds to the surface coverage of the thyroxine. The calibrated titration curve can be fitted by a Langmuir isotherm, using a 1:1 stoichiometry (FIG. 4C, inset) (Duan et al., 2012, Nat. Nanotechnol., 7: 401-407; Chang et al., 2011, ACS Nano, 5: 9883-9891). From this, an affinity constant (K) for d-thyroxine of $K=(7.11\pm1.95)\times10^8$ M$^{-1}$ can be determined. Surface titration with l-thyroxine was performed in a similar manner (with l-thyroxine concentrations of 2, 5, 10, 20, 25, 30, and 40 μM), and the resulting curve is shown in FIG. 4D. The calibrated maximum sensor response ($\Delta I/g_m$, surface potential change) is comparable with the d-thyroxine (although for much higher concentrations), which indicates the similar surface coverage of the bound thyroxine. By fitting the titration curve, the affinity constant for l-thyroxine is obtained as $K=(1.02\pm0.11)\times10^5$ M$^{-1}$. It is also noticed that a surprising higher affinity is obtained between the d-thyroxine and the CD-SAMs compared with its l-enantiomer (around 7000 times). Similar affinity results were reported by SPR measurement as well (Shahgaldian et al, 2005, J. Inclusion Phenom. Macrocyclic Chem., 53: 35-39). Such a higher affinity difference is likely due to the deep inclusion of the hydrophobic part of thyroxine in the lipophilic cavity of the cyclodextrin skeleton such that the chiral center and the polar functions of thyroxine are segregated outside the macrocycle (Easton et al., 1996, Chem. Soc. Rev., 25: 163-170).

To demonstrate β-CD-functionalized Si NWFETs as reversible sensors for protein detection, orthogonal linkers need to be developed that contain the protein-binding ligand and guest moieties that enable linking to the β-CD SAM. The linker has to be stable during protein sensing and with the potential for stimulated desorption. Here adamantane (Ad) groups was chosen as the guest sites. The Ad-β-CD interactions have been well characterized, and it was found that by choosing the correct number of Ad moieties, it is possible to control the thermodynamics, kinetics, and stoichiometry of the adsorption and desorption for such host-guest interactions (Ludden et al., 2006, Chem. Soc. Rev., 35: 1122-1134).

Figure 5B:
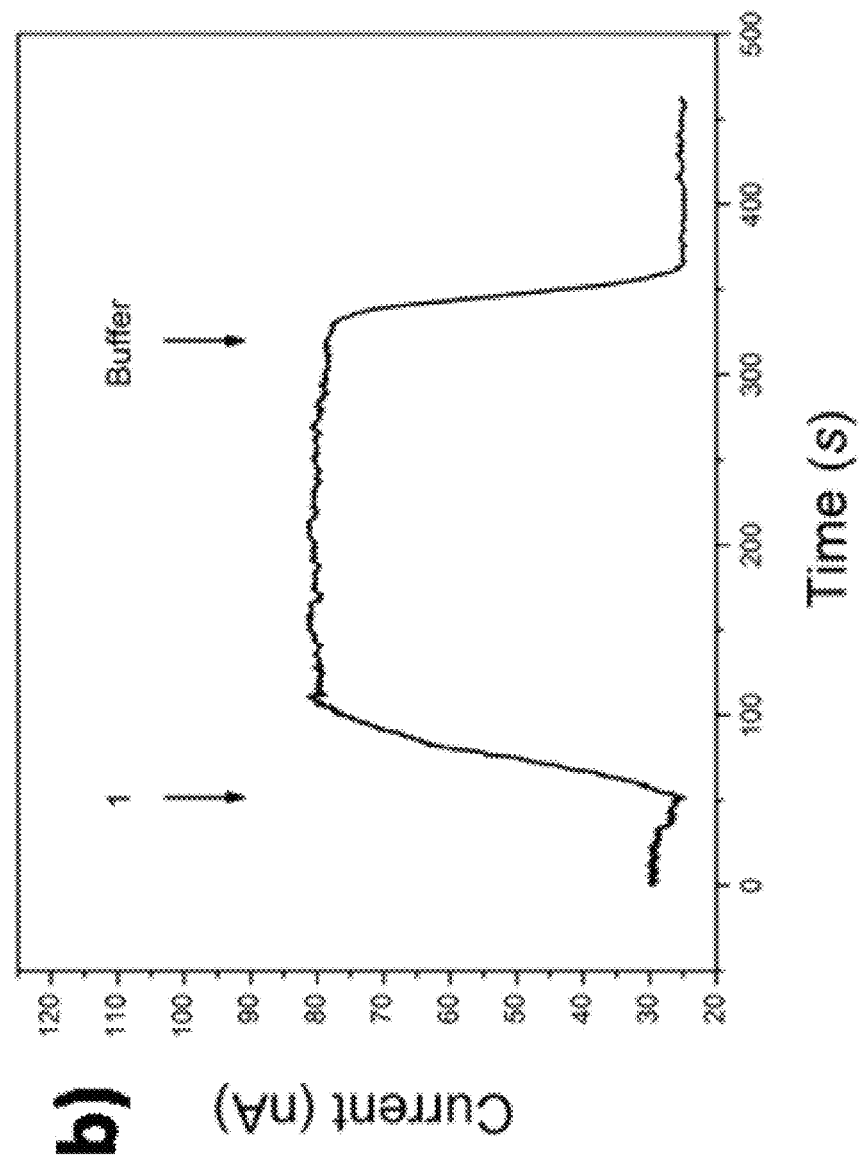
Figure 5C:
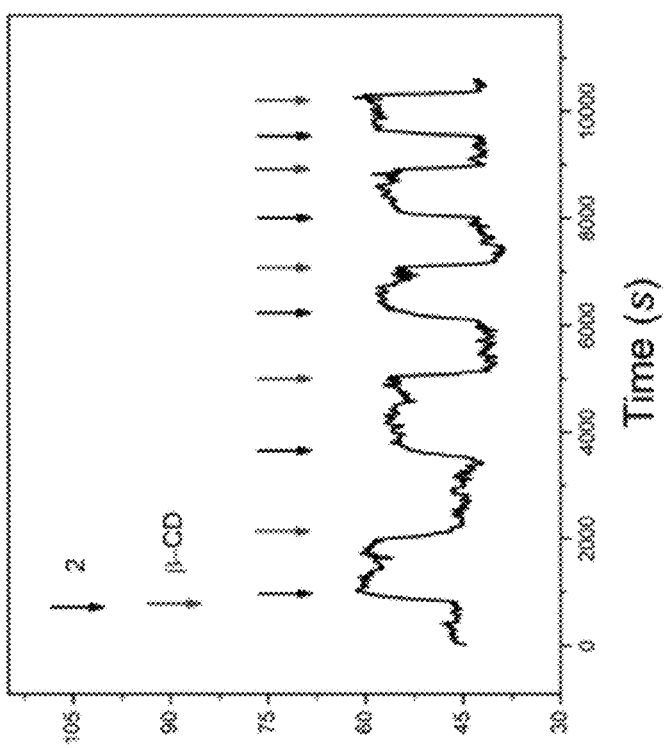
Figure 5D:
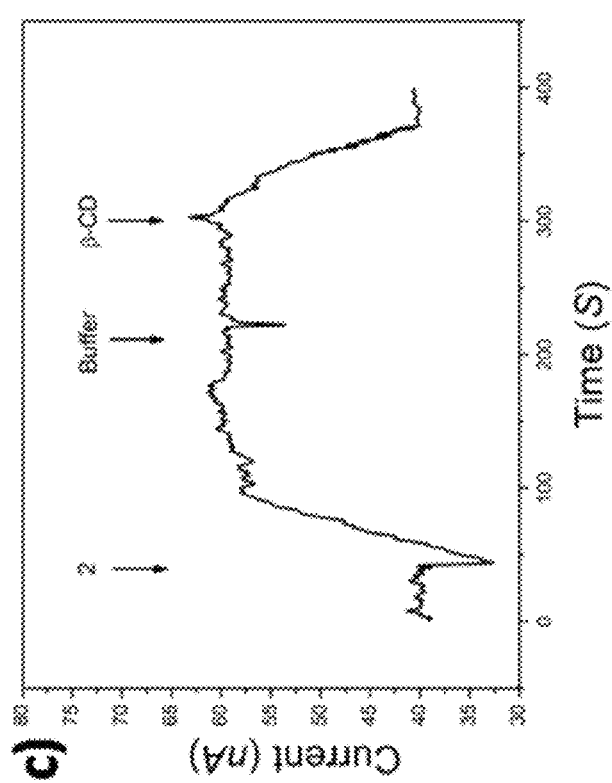

To test the stability and reversibility of the Ad-β-CD interactions, two guest molecules with either one or two Ad functionalities (which enable monovalent or divalent interactions with β-CD) were used to bind with β-CD SAMs (FIG. 5A). After injection, both molecules showed rapid adsorption on CD-NWs, as shown by the increase in current, corresponding to a negatively charged layer as a result of complexation. However, the monovalent complex 1 is not stable upon rinsing with buffer (FIG. 5B), whereas the divalent guest 2 is stable with buffer wash (FIG. 5C). This indicates the formation of kinetically stable assemblies due to the multivalent host-guest interactions, which agrees with the previous SPR measurements (Ludden et al., 2006, Chem. Soc. Rev., 35: 1122-1134). The guest molecules' adsorption was also monitored through fluorescence microscopy, which was consistent with the electrical observations (FIG. 10). To break the kinetically stable assembly, a competitive desorption approach was employed. Compound 2 can be completely desorbed from the CD-SAM with application of 8 mM β-CD, as shown by the fully restored baseline current (FIG. 5C). It is noted that from the previous SPR and fluorescent measurements desorption of the divalent molecules is normally not complete (Onclin et al., 2004, Langmuir, 20: 5460-5466). In contrast, a rapid and complete desorption of the divalent guest from the Si NWFETs was observed. Multiple adsorption and desorption cycles of compound 2 were also tested with the CD-NWs, and complete reversibility of the binding process of the divalent guest molecules could be demonstrated multiple times by the addition of β-CD (FIG. 5D). The desorption process is observed to be highly selective, rapid, and reversible without compromising the performance of the Si-NWs. These results indicate that the divalent Ad groups create stable assemblies at the CD surface that could be removed only by rinsing with a competitive β-CD solution, which is ideal as the building block of the orthogonal linker for protein sensing.

By employing this reversible, "cleavable" system, a heterobifunctional cross-linker can be designed that can work with any binding affinity system, even very strong binding systems that are considered irreversible (such as biotin-streptavidin (SAv)). Using this approach, the detection of biotin-SAv and subsequent reversibility by removal at the β-CD SAM it is shown herein. An orthogonal linker 3 (FIG. 6A) is developed, which consists of two Ad functionalities to ensure stable binding to CD-NWs and a biotin functionality to ensure binding to SAv. Three oligo(ethylene glycol) (OEG) chains were incorporated in the linker to increase the solubility of the Ad groups and prevent nonspecific protein binding.

Figure 12A:
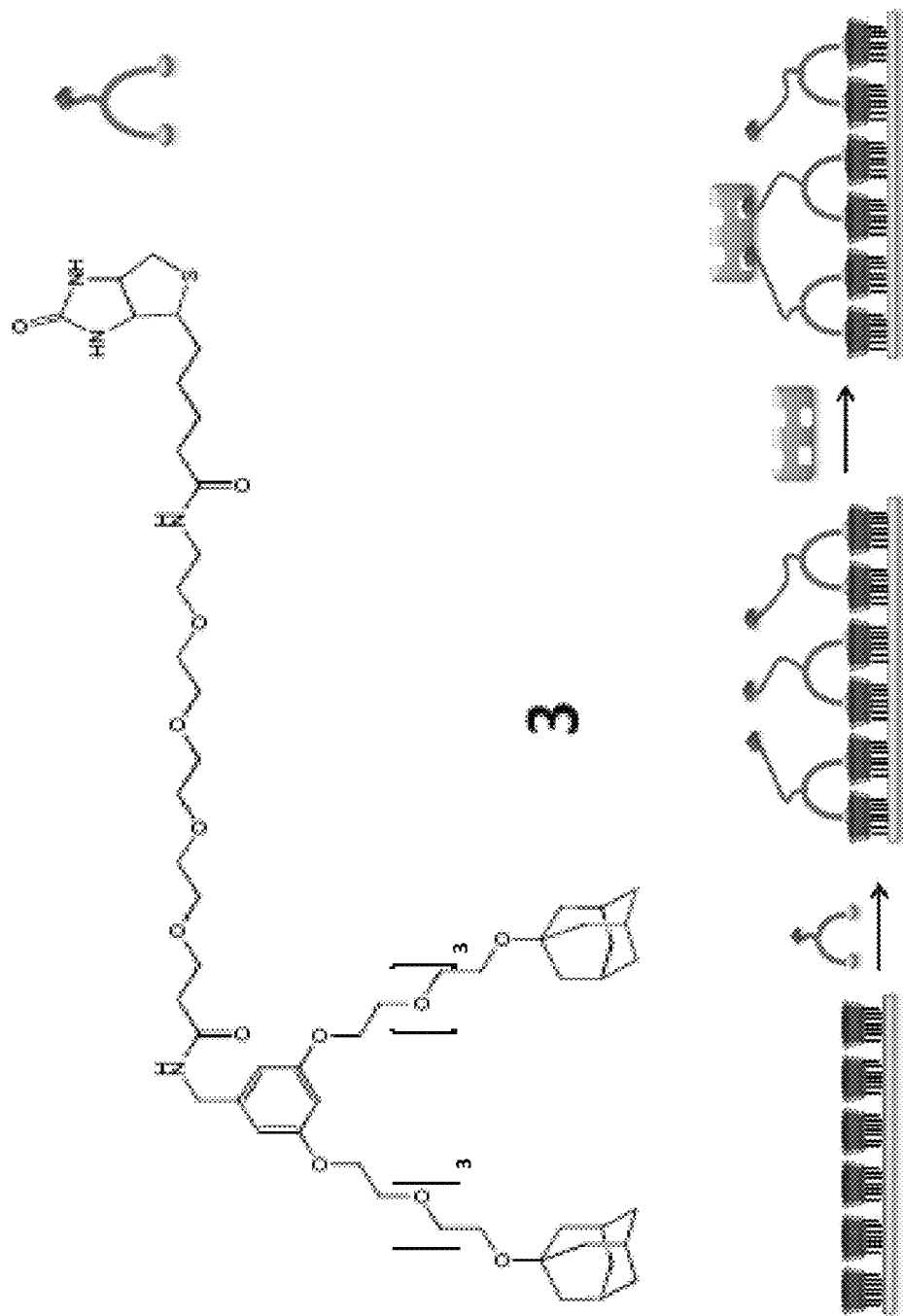
FIG. 12A and FIG. 12B, depicts the results of exemplary experiments.
Figure 12B:
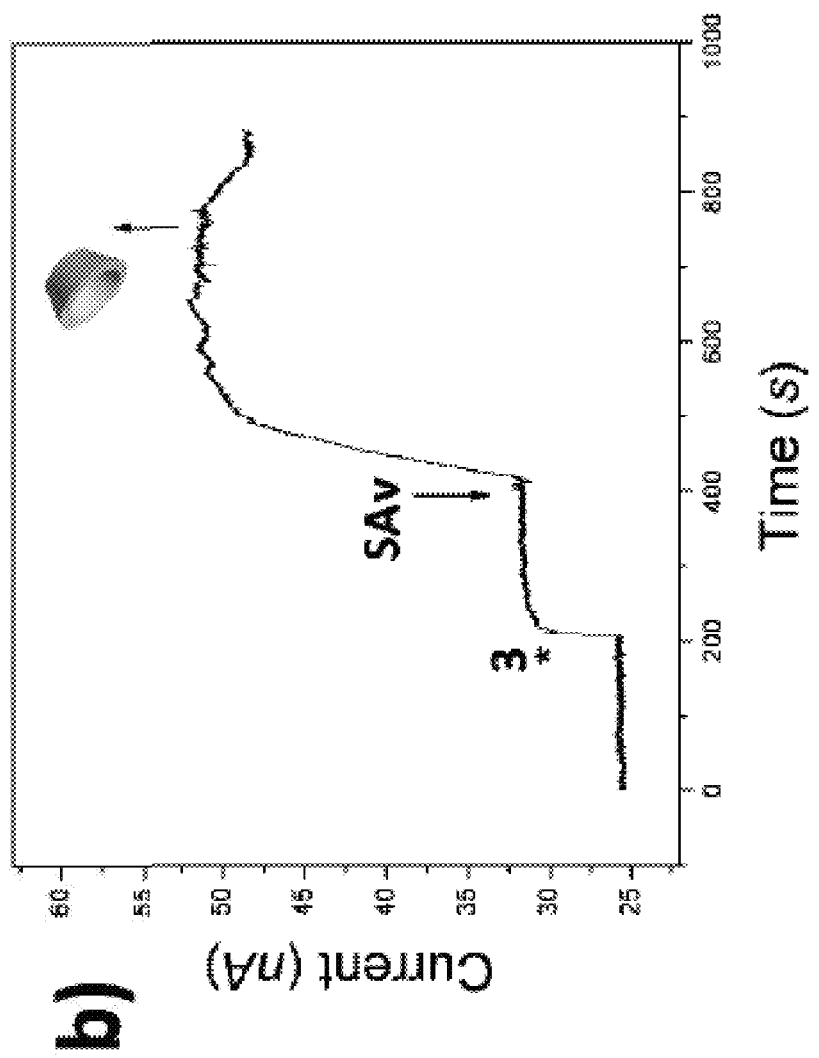

Experiments were conducted for detecting biotin-streptavidin (SAv) binding using only orthogonal linker 3. FIG. 12A shows the chemical structure of the divalent linker 3, and scheme of the adsorption of SAv. First, 5 µM of divalent linker 3 was adsorbed on the CD-NR, which was experimentally confirmed by an increase in the current due to the negatively charged biotin moieties (FIG. 12B). After the biotinylation, 2 nM of SAv was introduced. The current increased quickly after contact with SAv which indicates the adsorption of SAv due to its negative charge at pH 7.4 (PI≈5.6). After equilibration, the solution was switched to 8 mM of β-CD in HEPES to competitive desorb the SAv-divalent linker complex on the CD-NR. However it is observed that most of the SAv complex remained after the attempted desorption with β-CD. Even after prolonged rinsing with β-CD solutions, it was not possible to remove such complex from the surface. This strong binding behavior of SAv through the divalent linker 3 can be explained by examining the valency of the SAv/linker complexes at the β-CD SAM. Since SAv is a homotetrameric protein with four identical biotin-binding sites, SAv can bind two equivalents of divalent linker 3, which means linking to the β-CD SAM through four Ad moieties. This tetravalency effect is expected to make the SAv bind to the β-CD SAM with very high affinity, which cannot be removed from the surface.

This effect highlights that an important consideration for full reversibility is appropriate control of the surface receptor density; otherwise, cleavage of the CD linker may not be efficient. For the biotin-SAv system, it was found that a ~20% biotin surface density was optimal for efficient reversibility (whereas 100% coverage created a layer resistant to cleavage; FIG. 12). To achieve this density, a supramolecular blocking agent, 4, was designed which has two Ad groups for a stable interaction with the β-CD SAMs and an OEG chain as "protein-resistant" to reduce nonspecific protein absorption. By mixing divalent linker 3 and blocking agent 4, surface biotin concentration was optimized to enable SAv to form a 1:1 complex with divalent linker 3; thus the SAv is linked to β-CD SAMs through a divalent binding, which will facilitate the subsequent competitive desorption. FIG. 6A shows the chemical structures of divalent linker 3 and blocking agent 4 and their assembly scheme on β-CD SAMs for SAv sensing.

Figure 6B:
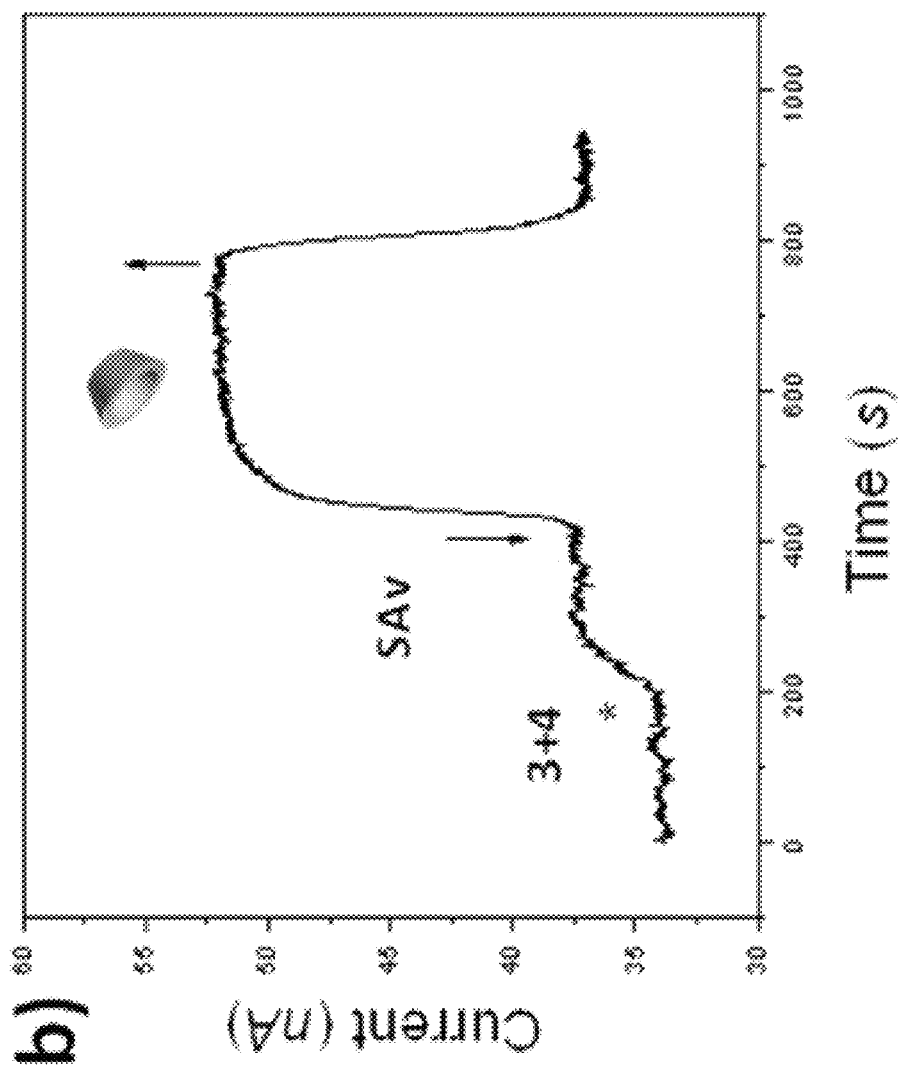
Figure 13:
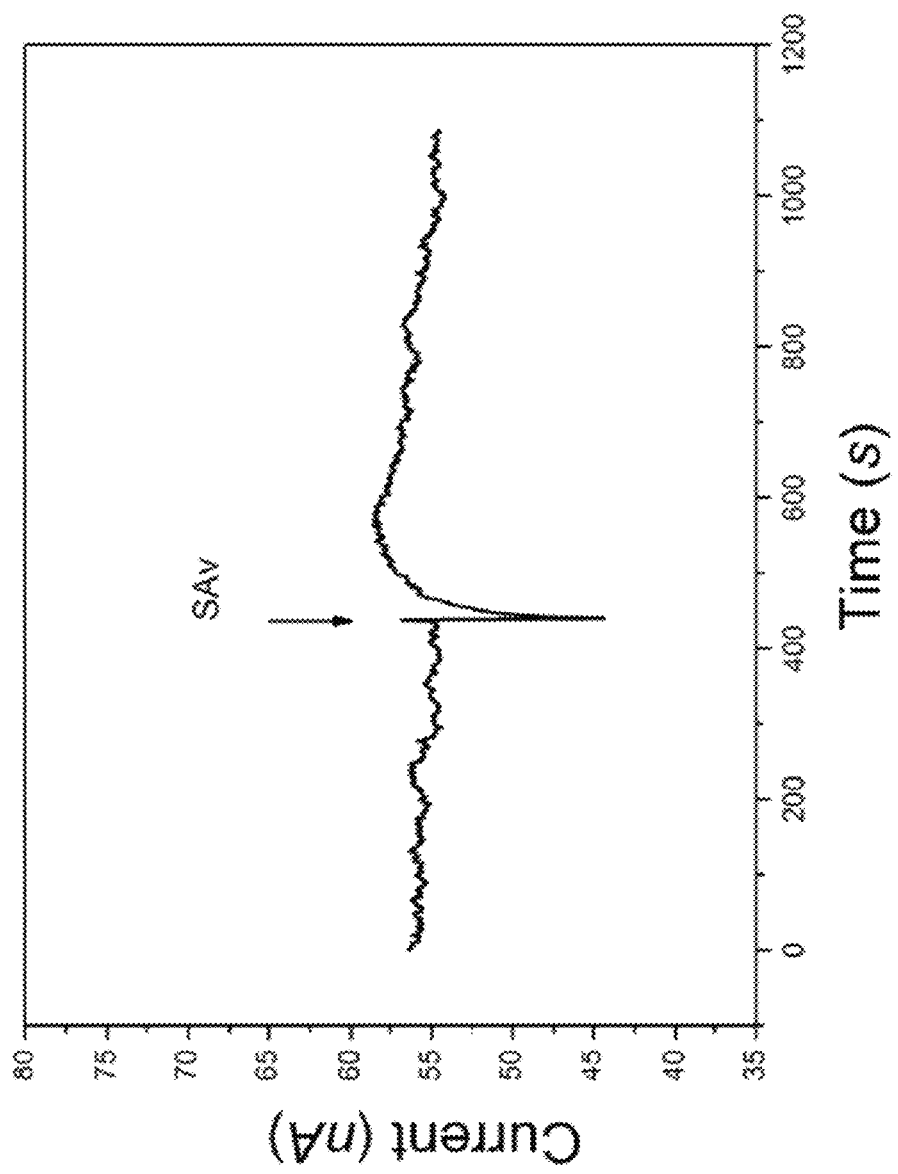
FIG. 13 is a graph depicting the results of a control experiment of biotin-blocked streptavidin (locked SAv) binding to CD functionalized Si NW after the divalent linker immobilization.

For SAv sensing, a mixture of divalent linker 3 and blocking agent 4 in HEPES buffer (5 µM, ratio 1:5, pH 7.4) was adsorbed on the Si NWFET, which was experimentally confirmed by an increase in the current due to the negatively charged biotin moieties (FIG. 6B). After the biotinylation, 2 nM SAv was introduced. Current increased quickly after contact with SAv, which indicates the adsorption of SAv is due to its negative charge at pH 7.4 (PI≈5.6). After equilibration, the solution was switched to 8 mM β-CD in HEPES, and the surface-bound SAv began to desorb, which was confirmed by a decrease in the current. Since this returns to the original baseline, it is concluded that the SAv desorption is almost complete. Less than 10% of the residue is left on the surface, which, while not wishing to be bound by any particular theory, is likely due to the uncontrolled tetravalent binding. Further decreasing the surface biotin concentration may reduce the possibility of the tetravalent binding; however, it will also lower the signal-to-noise ratio due to the smaller coverage of SAv. As a negative control, biotin-blocked streptavidin (locked SAv) was also injected under the same conditions, and no interaction was detected (FIG. 13), which indicates that the sensor response proceeded only through specific interactions of SAv and surface-immobilized biotin. The demonstrated reversible binding of SAv on β-CD-functionalized Si NWFETs will allow the reuse of the β-CD-functionalized surfaces for multiple detections. Furthermore, the stepwise adsorption of SAv through the supramolecular linker enables the free biotin binding pockets of SAv that are directed toward the solution, which could be used for binding of other biotinylated (bio)molecules toward multidisciplinary protein detection.

Demonstrated herein is a supramolecular interface for Si NWFET biosensors. The Si-NWs were successfully functionalized with β-CD SAMs. These devices have been used to detect thyroxine molecules through host-guest interactions and were able to discriminate between d and l enantiomers of thyroxine, which is the first demonstration that the Si NWFETs can be used as stereoselective sensors to analyze enantiomeric compositions. β-CD-functionalized Si NWFETs were also used to detect the biotin-streptavidin interactions through small, orthogonal, multivalent linker molecules. By choosing the appropriate number and type of guest sites, it is possible to control the adsorption and desorption of molecule assemblies at such an interface. The demonstrated reversible sensing of SAv with Si NWFETs represents a versatile, promising approach for the development of regenerative electronic biosensors, which are very attractive from both a device performance and economical point of view, since it permits accurate calibration prior to measurements and repeated use of the same calibrated device. The supramolecular interface and sensing method developed herein on Si NWFETs can be used broadly in fundamental research and benefit real device applications, enhancing sensor lifetime, reliability, and repeatability.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method of replacing a receptor molecule functionalized on a nanostructure of a regenerative nanosensor device comprising:
    providing the regenerative nanosensor device comprising the nanostructure forming an electrically conducting pathway between at least a first contact and a second contact, a nanostructure surface having a first coating comprising a reversible functionalized supramolecular assembly comprising a first receptor molecule; and
    disrupting the supramolecular assembly of the first coating to induce a selective removal of at least one layer of the first coating, thereby forming an unfunctionalized nanostructure.

2. The method of claim 1 comprising coating the unfunctionalized nanostructure with a second coating comprising a reversible functionalized supramolecular assembly comprising a second receptor molecule.

3. The method of claim 1, wherein the first coating comprises a self-assembled monolayer (SAM).

4. The method of claim 3, wherein the SAM comprises β-cyclodextrin (β-CD), thereby providing a β-CD SAM.

5. The method of claim 4, wherein disrupting the supramolecular assembly of the first coating comprises administering a solution to the device, wherein the solution comprises β-CD to induce the desorption of the linker from the SAM.

6. The method of claim 3, wherein the SAM comprises a polyelectrolyte thin film.

7. The method of claim 6, wherein disrupting the supramolecular assembly of the first coating comprises altering the pH of a solution surrounding the nanostructure to induce the desorption of the polyelectrolyte thin film.

8. The method of claim 1, wherein the first coating comprises a linker layer comprising a linker comprising a receptor molecule.

9. The method of claim 8, wherein the linker comprises a chain region which prevents non-specific binding to the nanostructure.

10. The method of claim 9, wherein the chain region comprises oligo(ethylene glycol) (OEG).

11. The method of claim 8, wherein the linker comprises a guest moiety which reversibly binds to the SAM.

12. The method of claim 11, wherein the guest moiety comprises adamantane.

* * * * *